United States Patent
Cheong et al.

(10) Patent No.: US 11,732,304 B2
(45) Date of Patent: Aug. 22, 2023

(54) SYSTEM FOR PREDICTING PROGNOSIS AND BENEFIT FROM ADJUVANT CHEMOTHERAPY FOR PATIENTS WITH STAGE II AND III GASTRIC CANCER

(71) Applicant: Novomics Co., Ltd., Seoul (KR)

(72) Inventors: Jae Ho Cheong, Seoul (KR); Sung Hoon Noh, Seoul (KR); Yong Min Huh, Seoul (KR); Hyun Ki Kim, Seoul (KR)

(73) Assignee: Novomics Co., Ltd., Seoul (KR)

( * ) Notice: Subject to any disclaimer, the term of this patent is extended or adjusted under 35 U.S.C. 154(b) by 497 days.

(21) Appl. No.: 16/345,710

(22) PCT Filed: Aug. 11, 2017

(86) PCT No.: PCT/KR2017/008781
§ 371 (c)(1),
(2) Date: Apr. 28, 2019

(87) PCT Pub. No.: WO2018/169145
PCT Pub. Date: Sep. 20, 2018

(65) Prior Publication Data
US 2019/0284637 A1    Sep. 19, 2019

(30) Foreign Application Priority Data
Mar. 14, 2017    (KR) .................. 10-2017-0032027

(51) Int. Cl.
*C12Q 1/6886*    (2018.01)
*C12Q 1/68*    (2018.01)

(52) U.S. Cl.
CPC ............ *C12Q 1/6886* (2013.01); *C12Q 1/68* (2013.01); *C12Q 2600/106* (2013.01); *C12Q 2600/118* (2013.01); *C12Q 2600/158* (2013.01)

(58) Field of Classification Search
CPC ............ C12Q 1/6886; C12Q 2600/106; C12Q 2600/118; C12Q 2600/158
See application file for complete search history.

(56) References Cited

U.S. PATENT DOCUMENTS

| | | |
|---|---|---|
| 2001/0029020 A1 | 10/2001 | Waldman et al. |
| 2016/0063179 A1 | 3/2016 | Huh et al. |
| 2016/0160290 A1 | 6/2016 | Huseni |

FOREIGN PATENT DOCUMENTS

| | | |
|---|---|---|
| KR | 10-2008-0063156 | 7/2008 |
| KR | 10-2012-0065959 | 6/2012 |
| KR | 10-2014-0011710 | 1/2014 |
| KR | 10-2014-0121522 | 10/2014 |
| KR | 10-2016-0058190 | 5/2016 |
| WO | WO 2005/007846 | 1/2005 |
| WO | WO 2009/045115 | 4/2009 |
| WO | WO 2015/172201 | 11/2015 |
| WO | WO 2018/169145 | 9/2018 |

OTHER PUBLICATIONS

Supplementary European Search Report and the European Search Opinion dated Mar. 27, 2020 From the European Patent Office Re. Application No. 17901292.7. (10 Pages).
Cho et al. "Gene Expression Signature-Based Prognostic Risk Score in Gastric Cancer", Clinical Cancer Research, XP055307553, 17(7): 1850-1857, Published Online Mar. 29, 2011.
Lee et al. "Development and Validation of A Six-Gene Recurrence Risk Score Assay for Gastric Cancer", Clinical Cancer Research, XP055677783, 22(24): 6228-6235, Published Online Sep. 21, 2016.
International Search Report and the Written Opinion dated Dec. 13, 2017 From the International Searching Authority Re. Application No. PCT/KR2017/008781.

*Primary Examiner* — Joseph G. Dauner

(57) ABSTRACT

The present invention relates to a system for predicting prognosis and benefit from adjuvant chemotherapy for patients with stage II and III gastric cancer, and an algorithm that can predict prognosis and chemotherapy responsiveness using quantitative analysis results of mRNA expression levels of a prognosis or chemotherapy responsiveness-related marker gene group and a reference gene group in advanced gastric cancer is developed, and can be used as supplementary information to determine a method for treating a gastric cancer patient.

6 Claims, 15 Drawing Sheets

Specification includes a Sequence Listing.

```
                  N    Observed    Expected    (O-E)^2/E    (O-E)^2/V
Cluster.all=1    24        5         11.0         3.24         3.60
Cluster.all=2   115       39         49.5         2.22         3.67
Cluster.all=3   168       84         67.6         4.00         8.61
   Chisq= 9.6 on 2 degrees of freedom, p = 0.00814
```

Fig. 15
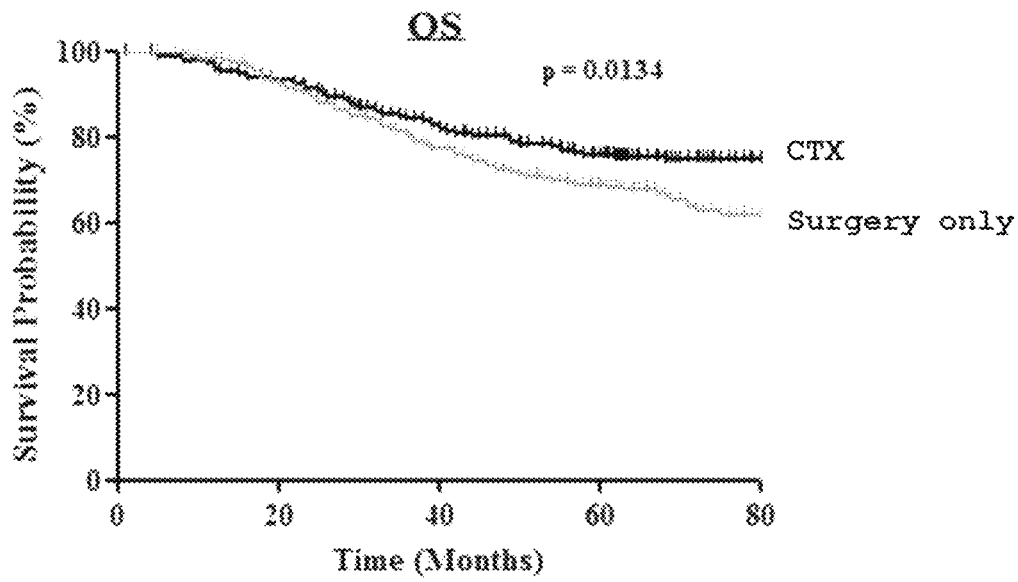
Fig. 16 (a)
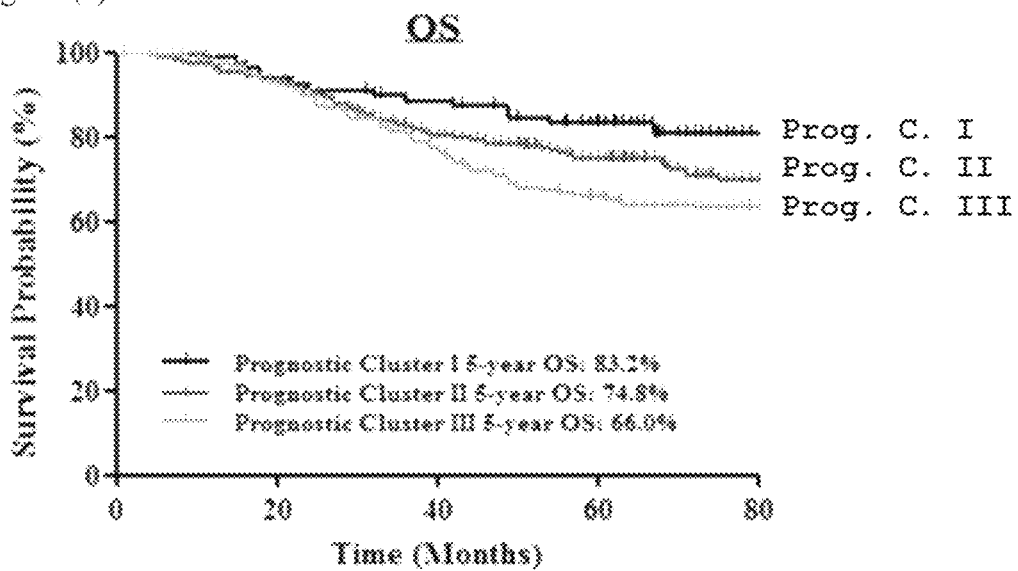
Fig. 16 (b)
|  | N | Observed | Expected | (O-E)^2/E | (O-E)^2/V |
|---|---|---|---|---|---|
| Cluster.all=1 | 79 | 14 | 34.2 | 4.280 | 4.99 |
| Cluster.all=2 | 296 | 78 | 84.2 | 0.459 | 0.89 |
| Cluster.all=3 | 250 | 83 | 66.6 | 4.033 | 6.55 |
Chisq= 8.8 on 2 degrees of freedom, p = 0.0121

Fig. 17
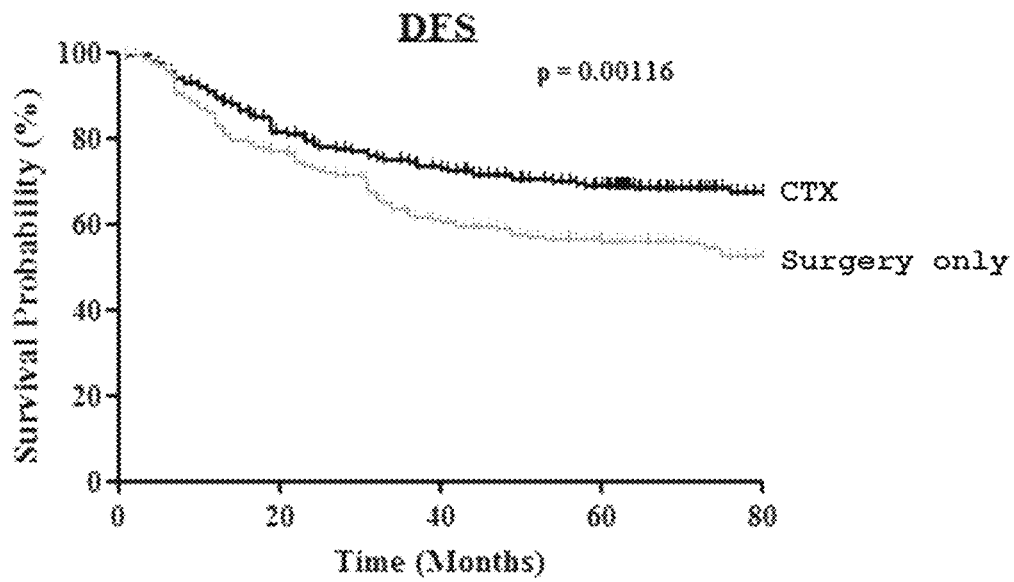
Fig. 18 (a)
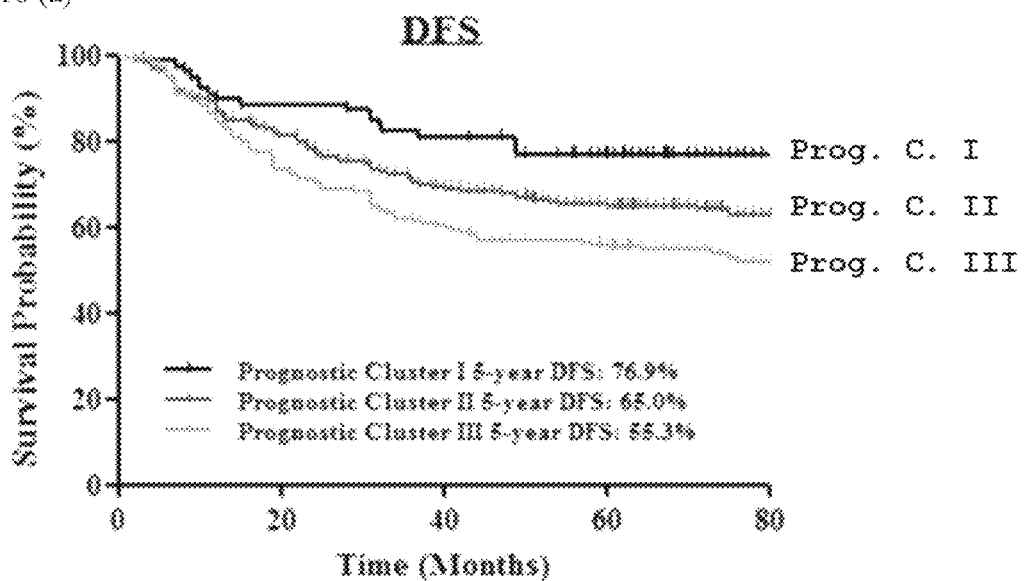
Fig. 18 (b)

SYSTEM FOR PREDICTING PROGNOSIS AND BENEFIT FROM ADJUVANT CHEMOTHERAPY FOR PATIENTS WITH STAGE II AND III GASTRIC CANCER

RELATED APPLICATIONS

This application is a National Phase of PCT Patent Application No. PCT/KR2017/008781 having International filing date of Aug. 11, 2017, which claims the benefit of priority of Korean Patent Application No. 10-2017-0032027 filed on Mar. 14, 2017. The contents of the above applications are all incorporated by reference as if fully set forth herein in their entirety.

SEQUENCE LISTING STATEMENT

The ASCII file, entitled 77521SequenceListing.txt, created on Apr. 27, 2019, comprising 5,374 bytes, submitted concurrently with the filing of this application is incorporated herein by reference. The sequence listing submitted herewith is identical to the sequence listing forming part of the international application.

FIELD AND BACKGROUND OF THE INVENTION

The present invention relates to a system for predicting prognosis and benefit from adjuvant chemotherapy for patients with advanced gastric cancer using quantitative analysis values of mRNA expression of a prognosis or chemotherapy responsiveness-related marker gene group and a reference gene group in patients with advanced gastric cancer.

Globally, gastric cancer is the third highest fatal cancer among all types of cancer, and particularly, the most common cancer except thyroid cancer which has a relatively good prognosis in Korea. In Korea, the survival rate of patients with gastric cancer has been significantly improved due to early detection by national medical checkups, surgical standardization and development of chemotherapy, but despite currently-standardized treatment, at least a half of patients with stage II and III advanced gastric cancer still experience recurrence.

Cancer has been recognized as a genetic disease, and there has been an effort to classify cancer according to its molecular and biological characteristics, rather than according to existing anatomical and pathological phenotypes, according to the development of genetic testing techniques such as Next Generation Sequencing (NGS). It has been recently reported that gastric cancer is broadly classified into four types according to various molecular characteristics in the Cancer Genome Atlas (TCGA) project. This means that, although cancer is anatomically at the same stage, prognosis and a degree of chemotherapy response may vary depending on its molecular and biological characteristics.

According to the recently-reported result of the TCGA project for 295 gastric cancer patients, gastric cancer is divided into four types including ① Epstein-Ban virus (EBV)-positive gastric cancer, ② microsatellite instability-high (MSI-H) gastric cancer, ③ chromosomal instability (CIN) gastric cancer, and ④ genomically-stable (GS) gastric cancer. According to such massive cancer genome sequencing, it can be known that the gastric cancer is classified into molecular genetically different subgroups, not a single type of cancer. Therefore, it shows that, for personalized treatment of gastric cancer, target genes need to be developed and applied according to subgroups based on molecular genetic and pathological characteristics. In addition, in the study of gastric cancer, the result in which prognosis can be classified according to subtypes of gastric cancer has been reported.

If the patient's prognosis can be predicted after chemotherapy following a gastric cancer surgery, it will be the evidentiary materials for establishing a suitable therapeutic strategy according to each prognosis. In current standardized treatment practices, adjuvant chemotherapy treatment after surgery has been used for all patients with stage II and III advanced gastric cancer. This therapy may be undertreatment in groups having a bad prognosis. That is, this may have a clinical meaning that can develop a strategy for additional therapeutic methods, other than the current standard treatment, with respect to patients having a bad prognosis.

In addition, as patients are divided into a chemotherapy-responder group (Predictive Cluster S) and a non-chemotherapy-responder group (Predictive Cluster R), detailed evidentiary data for establishing a patient therapeutic strategy may be provided by providing information of existing therapeutic methods in connection with the prognostic information. That is, overtreatment continuously using a conventional chemotherapy may be prevented for a non-chemotherapy-responder group (Predictive Cluster R) and a good prognostic group (Prognostic Cluster I), the use of a conventional therapeutic method may be urged for a chemotherapy-responder group (Predictive Cluster S), and classification that can induce the active development of a new therapeutic method is possible for a non-chemotherapy-responder group (Predictive Cluster R) and a bad prognostic group (Prognostic Cluster III).

Since 2010, it was found that, in the case of stage II and III advanced gastric cancer, adjuvant chemotherapy following standardized D2 gastrectomy increases the survival rate of a gastric cancer patient, and it is currently a standard therapy. Traditionally, gastric cancer is classified according to anatomical and pathological phenotypes, and when the gastric cancer is determined as stage 2 or higher according to TNM classification, chemotherapy treatment is used, but other than the TNM stage, there is no method for predicting prognosis according to chemotherapy treatment.

SUMMARY OF THE INVENTION

An object of the present invention provides a composition for predicting prognosis of advanced gastric cancer or chemotherapy responsiveness using analysis values for a marker gene group which is able to predict postoperative prognosis or chemotherapy responsiveness in patients with advanced gastric cancer (stage II-stage III: based on AJCC $6^{th}$ ed.) and a reference gene group.

Another object of the present invention provides a method for providing information to predict prognosis or chemotherapy responsiveness in terms of the survival rate of a patient using analysis values for a marker gene group which is able to predict postoperative prognosis or chemotherapy responsiveness in patients with advanced gastric cancer and a reference gene group.

To achieve the objects, the present invention provides a composition for predicting prognosis or chemotherapy responsiveness of stage II and III gastric cancer, which includes:

an agent for measuring an mRNA expression level in a prognosis or chemotherapy responsiveness-related marker gene group including WARS, GZMB, CDX1 and SFRP4; and an agent for measuring an mRNA expression level in a reference gene group including ACTB, ATP5E, GPX1, UBB and HPRT1.

The present invention also provides a kit for predicting prognosis or chemotherapy responsiveness of stage II and III gastric cancer, the kit including the composition for predicting prognosis or chemotherapy responsiveness of stage II and III gastric cancer.

The present invention also provides a method for providing information for predicting prognosis of stage II and III gastric cancer, the method including:

measuring mRNA expression levels of a prognosis or chemotherapy responsiveness-related marker gene group including WARS, GZMB, CDX1 and SFRP4, and a reference gene group including ACTB, ATP5E, GPX1, UBB and HPRT1 from a biological sample obtained from a tumor of stage II and III gastric cancer, and calculating ΔCq values of prognosis or chemotherapy responsiveness-related marker genes according to Equation 1 below; and in comparison with final threshold values of predetermined reference prognosis or chemotherapy responsiveness-related marker genes, classifying a group as a good prognostic group (Prognostic Cluster I) when ΔCq values of GZMB and WARS in the biological sample are higher than the final threshold values of predetermined reference GZMB and WARS, and provided that at least one ΔCq value of GZMB and WARS in the biological sample is lower than the final threshold value of predetermined reference GZMB or WARS, classifying a group as an intermediate prognostic group (Prognostic Cluster II) when the ΔCq value of SFRP4 in the biological sample is lower than the final threshold value of predetermined reference SFRP4, and a group as a bad prognostic group (Prognostic Cluster III) when the ΔCq value of SFRP4 in the biological sample is higher than the final threshold value of predetermined reference SFRP4, wherein the final threshold values of predetermined reference prognosis or chemotherapy responsiveness-related marker genes are −2.14, −5.18, −2.69 and −3.63 with respect to WARS, GZMB, CDX1 and SFRP4, respectively, and the final threshold value is calculated by obtaining ΔCq values of prognosis or chemotherapy responsiveness-related marker genes including WARS, GZMB, CDX1 and SFRP4 from tumor tissue samples of stage II and III gastric cancer, calculating an adaptive regression value per gene using the ΔCq value, and adding a correction value per gene to the adaptive regression value, the adaptive regression values of WARS, GZMB, CDX1 and SFRP4 are −2.54, −5.58, −3.59 and −4.53, respectively, and the correction values thereof are +0.4, +0.4, +0.9 and +0.9, respectively.

$$\Delta Cq = (Cq \text{ value of reference gene group}) - (Cq \text{ value of prognosis or chemotherapy responsiveness-related marker gene})$$ [Equation 1]

Here, the Cq value of the reference gene group refers to an average Cq value of reference genes including ACTB, ATP5E, GPX1, UBB and HPRT1.

The present invention also provides a method for providing information to predict chemotherapy responsiveness in stage II and III gastric cancer, the method including:

measuring mRNA expression levels of a prognosis or chemotherapy responsiveness-related marker gene group including WARS, GZMB, CDX1 and SFRP4 and a reference gene group including ACTB, ATP5E, GPX1, UBB and HPRT1 in a biological sample obtained from a tumor of stage II and III gastric cancer, and calculating ΔCq values of prognosis or chemotherapy responsiveness-related marker genes according to Equation 1 below; and in comparison with final threshold values of predetermined reference prognosis or chemotherapy responsiveness-related marker genes, classifying a group as a non-chemotherapy-responder group (Predictive Cluster R) when ΔCq values of GZMB and WARS in the biological sample are higher than the final threshold values of predetermined reference GZMB and WARS, and provided that at least one ΔCq value of GZMB and WARS in the biological sample is lower than the final threshold value of predetermined reference GZMB or WARS, classifying a group as a non-chemotherapy-responder group (Predictive Cluster R) when the ΔCq value of CDX1 in the biological sample is lower than the final threshold value of predetermined reference CDX1, and a group as a chemotherapy-responder group (Predictive Cluster S) when the ΔCq value of CDX1 in the biological sample is higher than the final threshold value of predetermined reference CDX1, wherein the final threshold values of predetermined reference prognosis or chemotherapy responsiveness-related marker genes, are −2.14, −5.18, −2.69 and −3.63 with respect to WARS, GZMB, CDX1 and SFRP4, respectively, and the final threshold value is calculated by obtaining ΔCq values of prognosis or chemotherapy responsiveness-related marker genes including WARS, GZMB, CDX1 and SFRP4 from tumor tissue samples of stage II and III gastric cancer, calculating an adaptive regression value per gene using the ΔCq value, and adding a correction value per gene to the adaptive regression value, the adaptive regression values of WARS, GZMB, CDX1 and SFRP4 are −2.54, −5.58, −3.59 and −4.53, respectively, and the correction values thereof are +0.4, +0.4, +0.9 and +0.9, respectively.

$$\Delta Cq = (Cq \text{ value of reference gene group}) - (Cq \text{ value of prognosis or chemotherapy responsiveness-related marker gene})$$ [Equation 1]

Here, the Cq value of the reference gene group refers to an average Cq value of reference genes including ACTB, ATP5E, GPX1, UBB and HPRT1.

In the present invention, an algorithm that can predict prognosis and chemotherapy responsiveness using quantitative analysis results of mRNA expression levels of a prognosis or chemotherapy responsiveness-related marker gene group and a reference gene group in advanced gastric cancer in terms of survival rates such as an overall survival rate and a disease-free survival rate is developed, and can be used as supplementary information to determine a method for treating a gastric cancer patient.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the attached drawings, in which:

FIG. 15 shows p values obtained from the Kaplan-Meier curves and log rank test for overall 5-year survival rates in a patient group that received Xeloda+oxaliplatin (XELOX) chemotherapy treatment (CTX) and an observation-only group (Surgery only) in a CLASSIC clinical trial sample.

FIGS. 16(a) and 16(b) show (a) Kaplan-Meir curves and (b) log rank test results for overall 5-year survival rates in a prognosis classification group with respect to a CLASSIC clinical trial sample according to the algorithm that can predict prognosis and chemotherapy responsiveness of advanced gastric cancer of the present invention.

FIG. 17 shows p values obtained from the Kaplan-Meier curves and log rank test for 5-year disease-free survival rates in a patient group that received Xeloda+oxaliplatin (XELOX) chemotherapy treatment (CTX) and an observation-only group (Surgery only) in a CLASSIC clinical trial sample.

FIGS. 18(a) and 18(b) show (a) Kaplan-Meir curves and (b) log rank test results for 5-year disease-free survival rates in the prognostic classification groups with respect to a CLASSIC clinical trial sample according to the algorithm that can predict prognosis and chemotherapy responsiveness of advanced gastric cancer of the present invention.

DESCRIPTION OF SPECIFIC EMBODIMENTS OF THE INVENTION

Figure 1:
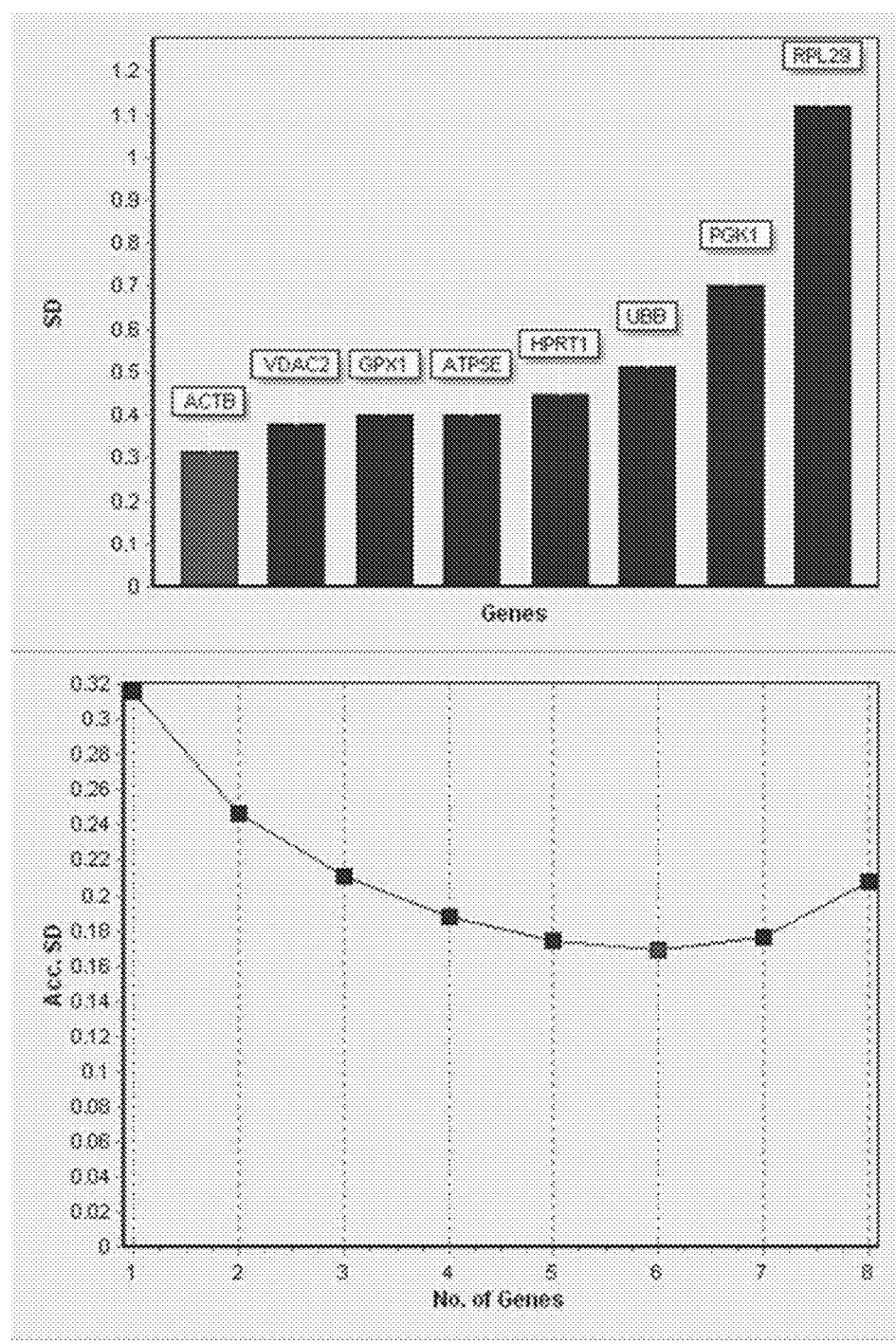
FIG. 1 shows the result of confirming an expression level of a target gene in a paraffin-embedded sample to select a reference gene.

Hereinafter, the configuration of the present invention will be described in detail.

The present invention relates to a composition for predicting prognosis or chemotherapy responsiveness of stage II and III gastric cancer, the composition including:

an agent for measuring an mRNA expression level in a prognosis or chemotherapy responsiveness-related marker gene group including WARS, GZMB, CDX1 and SFRP4; and an agent for measuring an mRNA expression level in a reference gene group including ACTB, ATP5E, GPX1, UBB and HPRT1.

The composition for predicting prognosis or chemotherapy responsiveness of stage II and III gastric cancer of the present invention may be used to predict prognosis and chemotherapy responsiveness in patients with advanced gastric cancer in terms of a survival rate.

The term "advanced gastric cancer" used herein refers to stage II or III gastric cancer based on AJCC 6$^{th}$ ed.

The term "prognosis or chemotherapy responsiveness-related marker gene" used herein refers to a marker that can distinguish between normal and pathological conditions, predict a 5-year survival rate after treatment, or objectively measure the prediction of treatment response. In the present invention, the marker gene is a gene that can be used to predict prognosis and chemotherapy responsiveness of advanced gastric cancer, and a gene that has a differential mRNA expression level which is increased or decreased according to prognosis or chemotherapy responsiveness. According to an exemplary embodiment of the present invention, a total of four marker genes for gastric cancer having heterogeneity are selected, wherein the marker genes are, for example, marker genes (WARS and GZMB) that can represent an immune module and marker genes (SFRP4 and CDX1) that can represent a stem-like module & an epithelial module, which are stably measured by ensuring statistical significance in microarray data and RT-qPCR data of fresh frozen tissue, and RT-qPCR data of a paraffin-embedded sample specimen.

The term "reference gene" used herein refers to a gene which is always stably expressed. That is, as a gene regularly expressed in any tissue, the reference gene is used to examine an expression level of a marker gene in comparison with its expression level. That is, since there is a qualitative difference between samples and a variation depending on a storage organization, even if a gene expression level is measured, it is difficult to determine that the measured value is a biological variation. Therefore, a gene expression level ($\Delta$Cq) between samples is determined by normalization. As conventional normalization methods, a method using a quantile, a global normalization method, and a method using a reference gene may be used, but in the present invention, normalization using a reference gene is used. In addition, the method using a single gene as a reference gene may be decreased in precision, and thus various genes may be selected and a variation degree may be investigated so as to select a reference gene suitable for the characteristics of tissue. In the present invention, a gene that is disclosed in literature associated with gastric cancer or utilized in a conventional commercialized product is selected, and the selected gene is proved whether or not to be suitable as an object, and then is used as a reference gene. According to an exemplary embodiment of the present invention, the 21 reference genes disclosed in the literature are compared to tissue of esophageal, pancreatic, gastric or colon cancer and normal tissue, and among them, a gene with the smallest variation is selected as a reference gene by qPCR. Subsequently, as reference genes used in commercialized products, ACTB, ATP5E, HPRT1, PGK1, GPX1, RPL29, UBB and VDAC2 are selected and subjected to qPCR, and finally, as reference genes used to predict the probability of prognosis or chemotherapy response of the advanced gastric cancer of the present invention, a group of genes ACTB, ATP5E, GPX1, UBB and HPRT1 is used.

The term "measurement of an mRNA expression level" used herein refers to measurement of an mRNA level by a process of confirming mRNA expression of prognosis or chemotherapy responsiveness-related marker genes or reference genes in a biological sample to predict the probability of prognosis or chemotherapy response of advanced gastric cancer. Methods for analyzing the mRNA expression include reverse transcription polymerase chain reaction (RT-PCR), competitive RT-PCR, real-time RT-PCR, RNase protection assay (RPA), Northern blotting, and a DNA chip, but the present invention is not limited thereto.

In the composition according to the present invention, the agent for measuring mRNA expression levels of prognosis or chemotherapy responsiveness-related markers genes and the reference genes includes a primer, probe or antisense nucleotide specifically binding to mRNA of the prognosis or chemotherapy responsiveness-related marker genes and the reference genes. Since information on the prognosis or chemotherapy responsiveness-related marker genes and the reference genes is known to GenBank, UniProt, etc., based on this information, a primer, probe or antisense nucleotide specifically binding to mRNA of a gene can be easily designed by one of ordinary skill in the art.

The term "primer" used herein is a fragment that recognizes a target gene sequence, and a primer pair that includes a pair of forward and reverse primers, but preferably, is a primer pair that provides an analysis result having specificity and sensitivity. Since the nucleic acid sequence of a primer is a sequence that is inconsistent with a non-target sequence present in a sample, when the primer is one that only amplifies a target gene sequence containing a complementary primer binding site and does not causes non-specific amplification, high specificity may be imparted. According to an exemplary embodiment of the present invention, a set of primers set forth in SEQ ID NOs: 1 to 18 may be used. More specifically, SFRP4 may be detected using a set of primers set forth in SEQ ID NOs: 1 and 2 with reference to NM_003014.2 1298-1361, GZMB may be detected using a set of primers set forth in SEQ ID NOs: 3 and 4 with reference to NM_004131.3 213-277, WARS may be detected using a set of primers set forth in SEQ ID NOs: 5 and 6 with reference to NM_173701.1 408-480, CDX1 may be detected using a set of primers set forth in SEQ ID NOs: 7 and 8 with reference to NM_001804.2 1319-1385, ACTB may be detected using a set of primers set forth in SEQ ID NOs: 9 and 10 with reference to NM_001101 278-349, ATP5E may be detected using a set of primers set forth in SEQ ID NOs: 11 and 12 with reference to NM_006886 117-189, HPRT1 may be detected using a set of primers set forth in SEQ ID NOs: 13 and 14 with reference to NM_000194.1 531-597, GPX1 may be detected using a set of primers set forth in SEQ ID NOs: 15 and 16 with reference to NM_000581.2 308-378, and UBB may be detected using a set of primers set forth in SEQ ID NOs: 17 and 18 with reference to NM_018955.2 61-138.

The term "probe" used herein refers to a material that can specifically bind to a target material to be detected in a sample to specifically identify the presence of a target material in a sample by the binding. The type of probe is one that is conventionally used in the art without limitation and may be a peptide nucleic acid (PNA), a locked nucleic acid (LNA), a peptide, a polypeptide, a protein, RNA or DNA. More specifically, the probe is a biomaterial, which may be derived from an organism, similar thereto or manufactured in vitro, for example, an enzyme, a protein, an antibody, a microorganism, animal or plant cells or organs (organelles), neurons, DNA, and RNA, DNA may include cDNA, genomic DNA, an oligonucleotide, RNA includes genomic RNA, mRNA, and an oligonucleotide, and a protein may include an antibody, an antigen, an enzyme, and a peptide. According to an exemplary embodiment of the present invention, probes of SEQ ID NOs: 19-27 for qPCR measurement may be used. Preferably, the probes may be fluorescent-labeled.

The term "antisense" used herein refers to an oligomer having a nucleotide base sequence and a backbone between subunits, the oligomer hybridized with a target sequence in RNA by forming Watson-Crick base pairs to typically allow formation of an RNA:oligomer heterodimer with mRNA in the target sequence. The oligomer may have exact sequence complementarity or approximate complementarity to a target sequence.

The term "prediction of prognosis or chemotherapy responsiveness" used herein includes determination of susceptibility of a subject to a specific disease or illness, prognosis of a subject with a specific disease or illness (e.g., identification of the condition of pre-metastatic or metastatic cancer, determination of the stage of cancer or responsiveness of cancer to treatment), or therametrics (e.g., monitoring of the condition of a subject to impart information on therapeutic efficacy). The object of the present invention is to predict prognosis and chemotherapy responsiveness in patients with gastric cancer after surgery in terms of survival rates such as an overall survival rate and a disease-free survival rate.

The composition for predicting prognosis or chemotherapy responsiveness of stage II and III gastric cancer according to the present invention may further include a pharmaceutically acceptable carrier.

The pharmaceutically acceptable carrier includes carriers and vehicles generally used in the pharmaceutical field, and specifically includes ion exchange resins, alumina, aluminum stearate, lecithin, serum proteins (e.g., human serum albumin), buffer materials (e.g., all types of phosphates, glycine, sorbic acid, potassium sorbate, and a partial glyceride mixture of saturated vegetable fatty acids), water, salts or electrolytes (e.g., protamine sulfate, disodium hydrogen phosphate, calcium hydrogen phosphate, sodium chloride and zinc salt), colloidal silica, magnesium trisilicate, polyvinyl pyrrolidone, a cellulose-based substrate, polyethylene glycol, sodium carboxymethyl cellulose, polyarylate, wax, polyethylene glycol or lanolin, but the present invention is not limited thereto.

In addition, the composition of the present invention may further include a lubricant, a wetting agent, an emulsion, a suspending agent or a preservative as well as the above-mentioned components.

The present invention also relates to a kit for predicting prognosis or chemotherapy responsiveness of stage II and III gastric cancer, the kit including the composition for predicting prognosis or chemotherapy responsiveness of stage II and III gastric cancer.

Preferably, the kit may be an RT-PCR kit or a DNA chip kit.

The kit for predicting prognosis or chemotherapy responsiveness of stage II and III gastric cancer may further include a composition, solution or device including one or more types of components, which is suitable for an analysis method. Preferably, the diagnosis kit may further include essential elements to perform RT-PCR. An RT-PCR kit includes primer pair specific to genes encoding marker proteins. A primer is a nucleotide having a sequence specific to the nucleic acid sequence of a gene, and may have a length of approximately 7 to 50 bp, and more preferably a length of approximately 10 to 30 bp. In addition, the RT-PCR kit may also include a primer specific to the nucleic acid sequence of a control gene. Other than these, the RT-PCR kit may include a test tube or another suitable container, reaction buffer solutions (various pH and magnesium concentrations), deoxynucleotides (dNTPs), enzymes such as a Taq-polymerase and a reverse transcriptase, DNase and RNase inhibitors, DEPC-water, and sterilized water.

In addition, the kit for predicting prognosis or chemotherapy responsiveness of stage II and III gastric cancer of the present invention may include essential elements to perform a DNA chip method. A DNA chip kit may include a substrate to which cDNA or oligonucleotide, which corresponds to a gene or fragments thereof, is attached, and reagents, agents, and enzymes for preparing fluorescence-labeled probes. In addition, the substrate may include cDNA or an oligonucleotide, which corresponds to a control gene or fragments thereof.

The present invention also provides a method for providing information to predict prognosis of stage II and III gastric cancer, the method including:

measuring mRNA expression levels of a prognosis or chemotherapy responsiveness-related marker gene group including WARS, GZMB, CDX1 and SFRP4, and a reference gene group including ACTB, ATP5E, GPX1, UBB and HPRT1 from a biological sample obtained from a tumor of stage II and III gastric cancer, and calculating $\Delta Cq$ values of prognosis or chemotherapy responsiveness-related marker genes according to Equation 1 below; and in comparison with the final threshold values of predetermined reference, prognosis or chemotherapy responsiveness-related marker genes, classifying a group as a good prognostic group (Prognostic Cluster I) when $\Delta Cq$ values of GZMB and WARS in the biological sample are higher than the final threshold values of predetermined reference GZMB and WARS, and provided that at least one $\Delta Cq$ value of GZMB and WARS in the biological sample is lower than the final threshold value of predetermined reference GZMB or WARS, classifying a group as an intermediate prognostic group (Prognostic Cluster II) when the $\Delta Cq$ value of SFRP4 in the biological sample is lower than the final threshold value of predetermined reference SFRP4, and a group as a bad prognostic group (Prognostic Cluster III) when the ΔCq value of SFRP4 in the biological sample is higher than the final threshold value of predetermined reference SFRP4, wherein the final threshold values of predetermined reference prognosis or chemotherapy responsiveness-related marker genes, are −2.14, −5.18, −2.69 and −3.63 with respect to WARS, GZMB, CDX1 and SFRP4, respectively, and the final threshold value is calculated by obtaining ΔCq values of prognosis or chemotherapy responsiveness-related marker genes including WARS, GZMB, CDX1 and SFRP4 from tumor tissue samples of stage II and III gastric cancer, calculating an adaptive regression value per gene using the ΔCq values, and adding a correction value per gene to the adaptive regression value, the adaptive regression values of WARS, GZMB, CDX1 and SFRP4 are −2.54, −5.58, −3.59 and −4.53, respectively, and the correction values thereof are +0.4, +0.4, +0.9 and +0.9, respectively:

ΔCq=(Cq value of reference gene group)−(Cq value of prognosis or chemotherapy responsiveness-related marker gene)   [Equation 1]

Here, the Cq value of the reference gene group refers to an average Cq value of reference genes including ACTB, ATP5E, GPX1, UBB and HPRT1.

The present invention also provides a method for providing information to predict chemotherapy responsiveness in stage II and III gastric cancer, the method including:

measuring mRNA expression levels of a prognosis or chemotherapy responsiveness-related marker gene group including WARS, GZMB, CDX1 and SFRP4 and a reference gene group including ACTB, ATP5E, GPX1, UBB and HPRT1 in a biological sample obtained from a tumor of stage II and III gastric cancer, and calculating ΔCq values of prognosis or chemotherapy responsiveness-related marker genes according to Equation 1 below; and in comparison with the final threshold values of predetermined reference prognosis or chemotherapy responsiveness-related marker genes, classifying a group as a non-chemotherapy-responder group (Predictive Cluster R) when ΔCq values of GZMB and WARS in the biological sample are higher than the final threshold values of predetermined reference GZMB and WARS, and provided that at least one ΔCq value of GZMB and WARS in the biological sample is lower than the final threshold value of predetermined reference GZMB or WARS, classifying a group as a non-chemotherapy-responder group (Predictive Cluster R) when the ΔCq value of CDX1 in the biological sample is lower than the final threshold value of predetermined reference CDX1, and a group as a chemotherapy-responder group (Predictive Cluster S) when the ΔCq value of CDX1 in the biological sample is higher than the final threshold value of predetermined reference CDX1, wherein the final threshold values of predetermined reference prognosis or chemotherapy responsiveness-related marker genes, are −2.14, −5.18, −2.69 and −3.63 with respect to WARS, GZMB, CDX1 and SFRP4, respectively, and the final threshold value is calculated by obtaining ΔCq values of prognosis or chemotherapy responsiveness-related marker genes including WARS, GZMB, CDX1 and SFRP4 from tumor tissue samples of stage II and III gastric cancer, calculating an adaptive regression value per gene using the ΔCq values, and adding a correction value per gene to the adaptive regression value, the adaptive regression values of WARS, GZMB, CDX1 and SFRP4 are −2.54, −5.58, −3.59 and −4.53, respectively, and the correction values thereof are +0.4, +0.4, +0.9 and +0.9, respectively:

ΔCq=(Cq value of reference gene group)−(Cq value of prognosis or chemotherapy responsiveness-related marker gene)   [Equation 1]

Here, the Cq value of the reference gene group refers to an average Cq value of reference genes including ACTB, ATP5E, GPX1, UBB and HPRT1.

The method for providing information to predict prognosis of stage II and III gastric cancer or chemotherapy responsiveness of the present invention will be described by step in detail.

The first step includes a step of measuring mRNA expression levels of a prognosis or chemotherapy responsiveness-related marker gene group and a reference gene group in a biological sample obtained from a tumor of stage II and III gastric cancer, and calculating a ΔCq value of each prognosis or chemotherapy responsiveness-related marker gene.

The mRNA expression levels of the prognosis or chemotherapy responsiveness-related marker gene group and the reference gene group may be measured by RT-PCR, competitive RT-PCR, real time RT-PCR, RNase protection analysis, Northern blotting or a DNA chip. More preferably, the mRNA expression level is measured by real time RT-PCR, or may obtain as a cycle quantitation (Cq) value.

A ΔCq value is calculated according to the following Equation 1 using the Cq values of the prognosis or chemotherapy responsiveness-related marker gene group obtained above and the reference gene group.

ΔCq=(Cq value of reference gene group)−(Cq value of prognosis or chemotherapy responsiveness-related marker gene)   [Equation 1]

Here, the Cq value of the reference gene group refers to an average Cq value of reference genes including ACTB, ATP5E, GPX1, UBB and HPRT1.

The ΔCq value refers to a value obtained by normalizing an expression level of a marker gene, and as the ΔCq value is higher, the expression level is higher.

The second step is a step of classifying prognostic groups of a biological sample in comparison with the final threshold values of predetermined reference prognosis or chemotherapy responsiveness-related marker genes.

To classify the prognostic groups, a final threshold value which becomes the standard of the prognosis or chemotherapy responsiveness-related marker genes is predetermined.

To this end, from a tumor tissue sample of stage II and III gastric cancer and a normal tissue sample, Cq values according to mRNA expression levels of the prognosis or chemotherapy responsiveness-related marker genes including WARS, GZMB, CDX1 and SFRP4 are obtained, a ΔCq value is calculated according to Equation 1, and an adaptive regression value (A.R.V.) is calculated by applying the ΔCq value to an adaptive regression technique. Generally, while data is processed based on a median or average of values selected by an array, in an algorithm according to the adaptive regression technique, a point having the largest variance of separated average interval values obtained when an arbitrary point of the total data is determined as a reference point is determined as an adaptive regression value (or a threshold value). That is, the threshold value is a reference point that distinguishes high expression and low expression of a corresponding gene, which are biologically significant, in normal and cancer tissue. The adaptive regression value is calculated as follows.

① Fitting by Adaptive Regression Method $$SSR = \sum_{i=1}^{n}(\hat{x}_i - \bar{x})^2 = SSTOT - SSE$$

$$MSR = SSR/(m-1)$$

$$MSB = SSB/(n-m)$$

$$F = \frac{MSR}{MSB}$$

wherein, SSR: Regression sum of squares; SSTOT: Total sum of squares; SSE: Sum of squares error; MSR: Regression mean square; MSB: Error mean square; and F: F-distribution.

Here, a p-value corresponding to the tail-probability of F-distribution is as follows.

$$P = Pr[F_{n-m}^{m-1} > F]$$

Wherein, $F_{n-m}^{m-1}$ is a random variable of F-distribution.

In the above-described process, as the p value is smaller, it can be considered that the fitting is better.

② Determination of Step Function $$F12 = \frac{(SSB_1 - SSB_2)/(m_2 - m_1)}{SSB_2/(n - m_2)}$$

Here, $F_{12}$ represents a relatively better fitting function between one step and two step.

③ In the method of the present invention, when an arbitrary point is determined as a reference point in total data by gene using the above-described one step method, a point at which statistics are the highest was determined as an A.R.V., and a correction value is added to the A.R.V. to determine a final threshold value.

Correction values of the marker genes may be obtained based on clinical usefulness and safety. That is, the correction values are determined by obtaining an A.R.V value, which is analytic performance, for a ΔCq value, and selecting a combination constituting the optimal hazard ratio in terms of prognosis and a combination constituting interactions between chemotherapy and predictive clusters in terms of chemotherapy responsiveness by screening a combination of 0.4 to 0.5 for WARS and GZMB, 0.8 to 0.9 for SFRP4 and 0.8 to 0.9 for CDX1 based on ΔCq for WARS, GZMB and SFRP4 constituting a prognosis axis and WARS, GZMB and CDX1 constituting a predictive axis.

Preferably, the adaptive regression values of WARS, GZMB, CDX1 and SFRP4 are −2.54, −5.58, −3.59 and −4.53, respectively, and the correction values thereof may be +0.4, +0.4, +0.9 and +0.9, respectively.

The marker genes, that is, the final threshold values of WARS, GZMB, CDX1 and SFRP4, which are obtained by adding correction values to the adaptive regression values, are −2.14, −5.18, −2.69 and −3.63, respectively.

When the final threshold values of the reference marker genes are determined, classification into prognostic groups and chemotherapy-responder groups (Predictive Cluster) is performed by a binary signal-based two-tier system. In other words, group classification according to an algorithm for predicting the probability of prognosis or chemotherapy response of the advanced gastric cancer of the present invention is specifically illustrated in FIG. 7, and refers to this, when the ΔCq values of GZMB and WARS in a biological sample are higher than the final threshold values of predetermined reference GZMB and WARS, the group is classified as a good prognostic group (Prognostic Cluster I), and provided that at least one ΔCq value of GZMB and WARS in the biological sample is lower than the final threshold value of predetermined reference GZMB or WARS, when the ΔCq value of SFRP4 in the biological sample is lower than the final threshold value of predetermined reference SFRP4, a group may be classified as an intermediate prognostic group (Prognostic Cluster II), and when the ΔCq value of SFRP4 in the biological sample is higher than the final threshold value of predetermined reference SFRP4, a group may be classified as a bad prognostic group (Prognostic Cluster III).

In addition, when the ΔCq values of GZMB and WARS in a biological sample are higher than the final threshold values of predetermined reference GZMB and WARS, a group is classified as a non-chemotherapy-responder group (Predictive Cluster R), and provided that at least one ΔCq value of GZMB and WARS in the biological sample is lower than the final threshold value of predetermined reference GZMB or WARS, when the ΔCq value of CDX1 in the biological sample is lower than the final threshold value of predetermined reference CDX1, a group is classified as a non-chemotherapy-responder group (Predictive Cluster R), and when the ΔCq value of CDX1 in the biological sample is higher than the final threshold value of predetermined reference CDX1, a group may be classified as a chemotherapy-responder group (Predictive Cluster S).

The biological sample may be fresh tumor tissue, fresh frozen tumor tissue, paraffin-embedded tumor tissue, a fine needle aspiration fluid, ascites, a tube washing solution, or a pleural fluid, and preferably, is paraffin-embedded tumor tissue.

In addition, the measurement of mRNA expression levels of the prognosis or chemotherapy responsiveness-related marker gene group and the reference gene group may be performed by RT-PCR, competitive RT-PCR, real time RT-PCR, RNase protection analysis, Northern blotting or a DNA chip. Preferably, the measurement is performed by real time RT-PCR.

Hereinafter, the advantages and characteristics of the present invention and the methods of accomplishing the same may be clearly understood by reference to the detailed description of exemplary embodiments and the accompanying drawings. However, the present invention is not limited to the exemplary embodiments disclosed below, and may be embodied in many different forms. These exemplary embodiments are merely provided to complete the disclosure of the present invention and fully convey the scope of the present invention to those of ordinary skill in the art, and the present invention should be defined by only the accompanying claims.

EXAMPLES

<Example 1> Development of Algorithm that Predicts Prognosis or Probability of Chemotherapy Responsiveness of Advanced Gastric Cancer A 3-mm pore including a 50% or more of a tumor was made in paraffin embedded tissue of advanced gastric cancer, and RNA was extracted from the perforated tissue according to a protocol. At least 400 ng of total RNA was obtained. A required Q.C element was A260/A280=>1.8.

For an RT-qPCR experiment, an nProfiler I kit was used, the total RNA (400 ng/18 μl) of a patient was used, and a gene specific primer (GSP) mix (3 μl) was dispersed in a sample. A temperature of a 2720 thermal cycler (Applied Biosystems) was increased to 50° C., and then a sample was put into the cycler. The RNA sample was denatured at 65° C. for 5 minutes, and the thermal cycler was stopped. For RT, 6 μl of RT buffer and 2 μl of an RT mix were added, DNA synthesis was performed at 37° C. for 60 minutes, and the DNA was maintained at 70° C. for 15 minutes. To perform qPCR, a cDNA mix (3 μl) and each of nine primer-probe mixes (2 μl, Gene-1 to Gene-9 from the kit) were mixed. The sample was subjected to one cycle of enzyme activation at 95° C. for 120 seconds, 40 cycles of denaturation at 95° C. for 10 seconds and detection at 60° C. for 30 seconds. The extracted data was analyzed using an nDxI program (Novomics Co., Ltd.).

The RT and qPCR processes were prepared by nProfiler I, and the nProfiler I is an mRNA-based qPCR kit consisting of 9 genes for gastric cancer. Reagents used herein are shown in Table 1.

TABLE 1 qPCR composition of nProfiler I kit

| KIT | Label | Purpose |
|---|---|---|
| KIT A | GSP MIX | RT-PCR |
| | RT buffer | RT-PCR |
| | RT MIX | RT-PCR |
| | qPCR MIC | qPCR |
| | Negative Control I | qPCR |
| | GENE-1 (SFRP4) Primer-Probe MIX | qPCR |
| | GENE-2 (GZMB) Primer-Probe MIX | qPCR |
| | GENE-3 (WARS) Primer-Probe MIX | qPCR |
| | GENE-4 (CDX1) Primer-Probe MIX | qPCR |
| | GENE-5 (ACTB) Primer-Probe MIX | qPCR |
| | GENE-6 (ATP5E) Primer-Probe MIX | qPCR |
| | GENE-7 (HPRT1) Primer-Probe MIX | qPCR |
| | GENE-8 (GPX1) Primer-Probe MIX | qPCR |
| | GENE-9 (UBB) Primer-Probe MIX | qPCR |
| KIT B | Positive Control I | RT-PCR |

| Gene | Type | Primer/Probe Sequence (5'-3') | SEQ ID NO. |
|---|---|---|---|
| SFRP4 (NM_003014.2) | Forward | ggagacttccgacttccttaca | 1 |
| | Reverse | tggccttacataggctgtcc | 2 |
| | Probe | aggcaatgcccagcctcatc | 19 |
| GZMB (NM_004131.3) | Forward | cggtggcttcctgatacaag | 3 |
| | Reverse | ttatggagcttccccaacag | 4 |
| | Probe | cgacttcgtgctgacagctgc | 20 |
| WARS (NM_173701.1) | Forward | ttgtggacccatggacagta | 5 |
| | Reverse | ccaaaccgaacaatgagctt | 6 |
| | Probe | tgccttttgcactgcttgtctg | 21 |
| CDX1 (NM_001804.2) | Forward | agggaggaacgtggtcaact | 7 |
| | Reverse | tatgatggggcaggtagaa | 8 |
| | Probe | tgcctcttcctgcagcctca | 22 |
| ACTB (NM_001101) | Forward | tcaccctgaagtaccccatc | 9 |
| | Reverse | tgtggtgccagattttctcc | 10 |
| | Probe | cggcatcgtcaccaactggg | 23 |
| ATP5E (NM_006886) | Forward | atggtggcctactggagaca | 11 |
| | Reverse | ctctcactgcttttgcacaga | 12 |
| | Probe | tggactcagctacatccgatactccca | 24 |
| HPRT1 (NM_000194.1) | Forward | tggtcaggcagtataatccaa | 13 |
| | Reverse | cttcgtggggtccttttcac | 14 |
| | Probe | tgcaagcttgcgaccttgacc | 25 |
| GPX1 (NM_000581.2) | Forward | cccgtgcaaccagtttgg | 15 |
| | Reverse | ggacgtacttgagggaattcaga | 16 |
| | Probe | ctcttcgttcttggcgttctcctgatg | 26 |
| UBB (NM_018955.2) | Forward | tgggtgagcttgtttgtgtc | 17 |
| | Reverse | tttgacctgttagcggatacc | 18 |
| | Probe | caccaaccacgtccacccac | 27 |

The above-mentioned 9 genes are four marker genes having statistical significance in microarray data and RT-qPCR data of fresh frozen tissue, and RT-qPCR data of a paraffin-embedded sample specimen and five reference genes. An nProfiler I stomach cancer assay, which is a diagnosis kit which can classify prognosis according to expression levels of the finally-selected genes, was developed.

A process of selecting reference genes is as follows.

Reference genes specifically applied to gastric cancer were subjected to a literature investigation through the following papers:

Identification of reference genes suitable for gene expression research in gastric cancer by RT-qPCR (Identification of valid reference genes for gene expression studies of human stomach cancer by reverse transcription-qPCR. Rho et al. BMC Cancer 2010, 10:240); change in reference gene in colorectal, esophageal and gastric cancer tissues (Housekeeping gene variability in normal and cancerous colorectal, pancreatic, esophageal, gastric and hepatic tissues. Claudia Rubie et al. *Mol Cell Probes*. 2005); case study for reference genes as US similar products using qPCR: breast cancer reference genes (A Multigene Assay to Predict Recurrence of Tamoxifen-Treated, Node-Negative Breast Cancer. Paik S et al. *N Engl J Med*. 2004 December); colorectal cancer reference genes (Interaction Between Tumor Gene Expression and Recurrence in Four Independent Studies of Patients With Stage II/III Colon Cancer Treated With Surgery Alone or Surgery Plus Adjuvant Fluorouracil Plus Leucovorin. O'Connell et al. *J Clin Oncol*. 2010).

In addition, reference genes, which are used in currently commercialized solid cancer-related products, were examined. A gene selected based on these genes was verified using preceding research whether the gene is suitable as a reference gene of a clinical sample, and finally selected.

On the basis of the above, primarily, a total of 8 reference genes were selected as candidates.

Finally, 5 genes which have the smallest variation degree when being combined in 30 paraffin-embedded samples were selected (using geNorm) as reference genes (refer to FIG. 1): ACTB/ATP5E/GPX1/UBB/HPRT1

Subsequently, to develop an algorithm, real time RT PCR was performed for 310 remaining paraffin-embedded sample specimens (3-mm core) obtained from patients with stage II or III gastric cancer, who had underwent surgery at Severance Hospital, Yonsei University in 2006 to 2010.

Marker genes are genes which can distinguish the heterogeneity of gastric cancer and can be stably detected in cancer tissue, and there are four marker genes, such as marker genes (WARS, GZMB) which can represent an immune axis, a marker gene (SFRP4) which can represent a stem-like axis, and a marker gene (CDX1) which can represent an epithelial axis.

The marker genes developed above and the reference genes described above are shown in Table 2 below.

TABLE 2

| Type | Axis | Type | Use |
|------|------|------|-----|
| WARS | Immune axis | ACTB | Reference gene |
| GZMB |  | ATP5E |  |
| CDX 1 | Epithelial axis | HPRT 1 |  |
| SFRP4 | Stem-like Axis | GPX 1 |  |
|  |  | UBB |  |

Afterward, threshold values per gene in the prognosis or chemotherapy responsiveness-related marker gene groups and reference gene groups were determined so as to establish a standard for classifying prognosis-associated groups (Prognostic Cluster I: good prognostic group, Prognostic Cluster II: intermediate prognostic group and Prognostic Cluster III: bad prognostic group) and chemotherapy responsiveness-associated groups (Predictive Cluster S: chemotherapy-responder group and Predictive Cluster R: non-chemotherapy-responder group).

To establish such a classification standard, the gene groups were classified into prognostic groups (Prognostic Clusters) and chemotherapy-responder groups (Predictive Clusters) using a binary signal-based two-tier system.

The ΔCq value of each marker gene was calculated according to Equation 1 below using the Cq values of the prognosis or chemotherapy responsiveness-related marker gene group and the reference gene group, which were obtained by real time RT-PCR, thereby normalizing an mRNA expression level:

$$\Delta Cq = Cq \text{ value of reference gene group} - Cq \text{ value of marker gene} \quad \text{[Equation 1]}$$

Here, the Cq value of the reference gene group refers to an average Cq value of reference genes including ACTB, ATP5E, GPX1, UBB and HPRT1.

As the ΔCq value is higher, gene expression is higher.

An adaptive regression value (A.R.V.) was calculated by applying the ΔCq value to an adaptive regression technique. Generally, while data was processed based on a median or average of values selected by an array, in an algorithm according to the adaptive regression technique, a point having the largest variance of separated average interval values obtained when an arbitrary point of the total data was determined as a reference point was determined as an adaptive regression value (or a threshold value). That is, the threshold value was a reference point that distinguishes high expression and low expression of a corresponding gene, which are biologically significant, in normal and cancer tissue. The adaptive regression value was calculated as follows.

① Fitting by Adaptive Regression Method $$SSR = \sum_{i=1}^{n} (\hat{x}_i - \bar{x})^2 = SSTOT - SSE$$

$$MSR = SSR/(m-1)$$

$$MSB = SSB/(n-m)$$

$$F = \frac{MSR}{MSB}$$

wherein, SSR: Regression sum of squares; SSTOT: Total sum of squares; SSE: Sum of squares error; MSR: Regression mean square; MSB: Error mean square; and F: F-distribution.

Here, a p-value corresponding to the tail-probability of F-distribution is as follows.

$$P = Pr[F_{n-m}^{m-1} > F]$$

Wherein $F_{n-m}^{m-1}$ is a random variable of F-distribution.

In the above-described process, as the p value is smaller, it can be considered that the fitting is better.

② Determination of Step Function $$F12 = \frac{(SSB_1 - SSB_2)/(m_2 - m_1)}{SSB_2/(n - m_2)}$$

Here, $F_{12}$ represents a relatively better fitting function between one step and two step.

Figure 2:
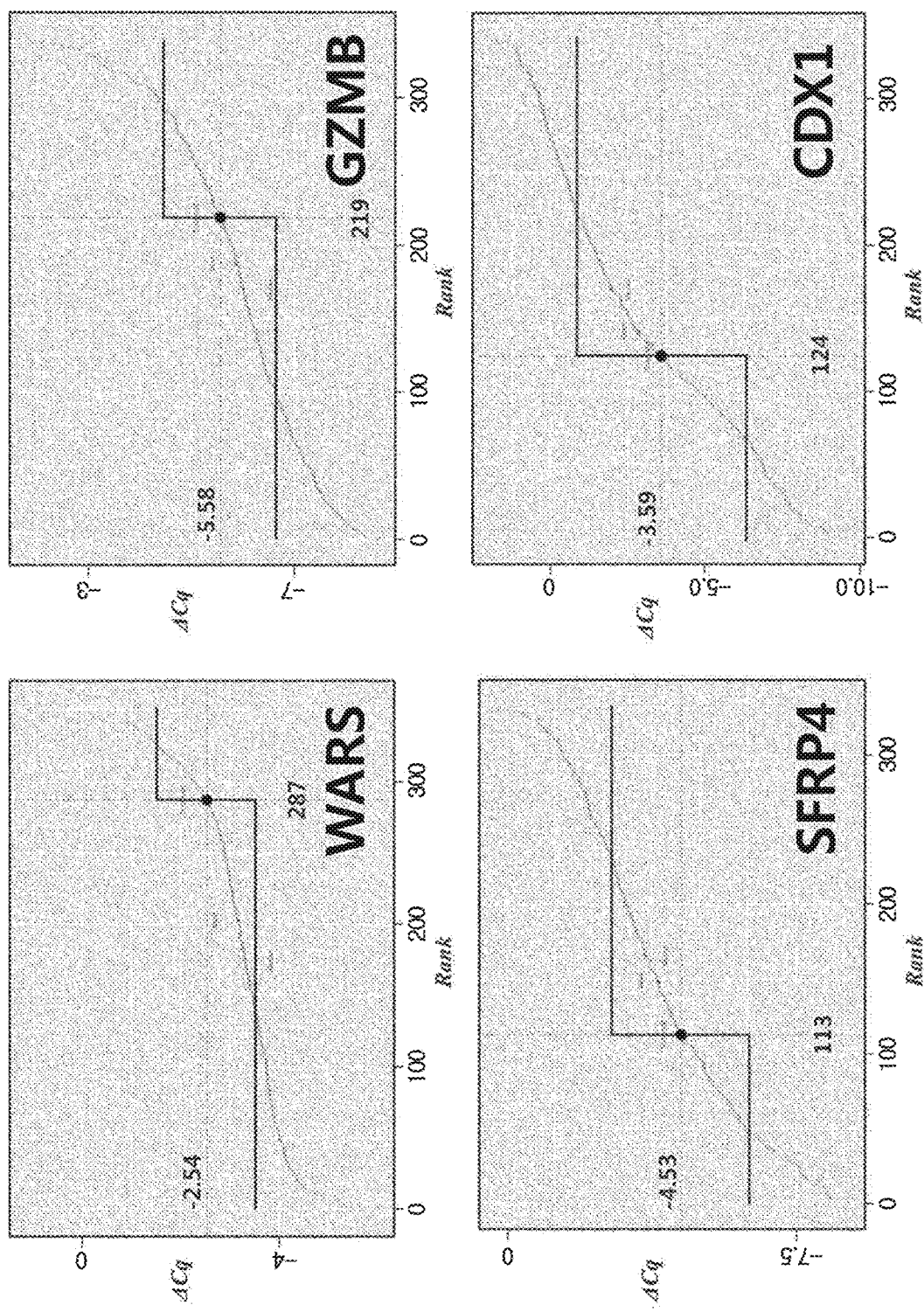
FIG. 2 shows ΔCq values representing adaptive regression value of prognosis and chemotherapy prediction-related marker genes, to which correction values +0.4, +0.4, +0.9 and +0.9 of WARS, GZMB, CDX1 and SFRP4 are added, respectively, to determine final threshold values.

③ In the method of the present invention, when an arbitrary point was determined as a reference point in total data by gene using the above-described one step method, a point at which statistics are the highest was determined as an A.R.V., and a correction value was added to the A.R.V. to determine a final threshold value. The A.R.V. was obtained for 310 tumor tissue paraffin-embedded samples and 108 normal tissue paraffin-embedded samples, and the normal tissue samples and the gastric cancer tissue samples were quantified and normalized. Values calculated for the normal and gastric cancer tissue samples per gene using an adaptive regression technique were obtained, final threshold values corresponding to the standards below were determined by applying the above-mentioned correction values to the values previously obtained. In addition, when the Cq value of a gene was determined as N/A or undetermined, the corresponding gene of this sample was eliminated from adaptive regression values. The final threshold values of the marker genes calculated according to the above-described method are shown in Table 3 below (refer to FIG. 2).

TABLE 3

| Marker gene | Adaptive regression value | Correction value | Final threshold value |
| --- | --- | --- | --- |
| WARS | −2.54 | +0.4 | −2.14 |
| GZMB | −5.58 | +0.4 | −5.18 |
| CDX1 | −3.59 | +0.9 | −2.69 |
| SFRP4 | −4.53 | +0.9 | −3.63 |

The binary signal-based two-tier system was classified using four marker genes as follows.

Figure 3:
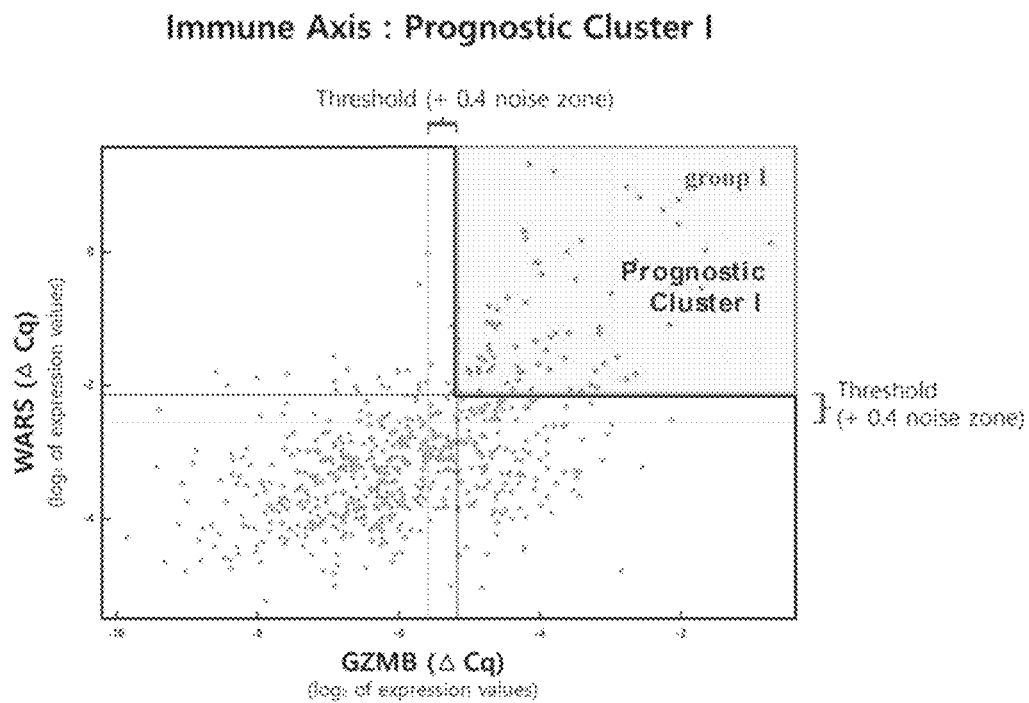
FIG. 3 shows a result illustrating a good prognostic group (Prognostic Cluster I) classified from an immune axis in the first tier of a binary signal-based two-tier system of the present invention.
Figure 4:
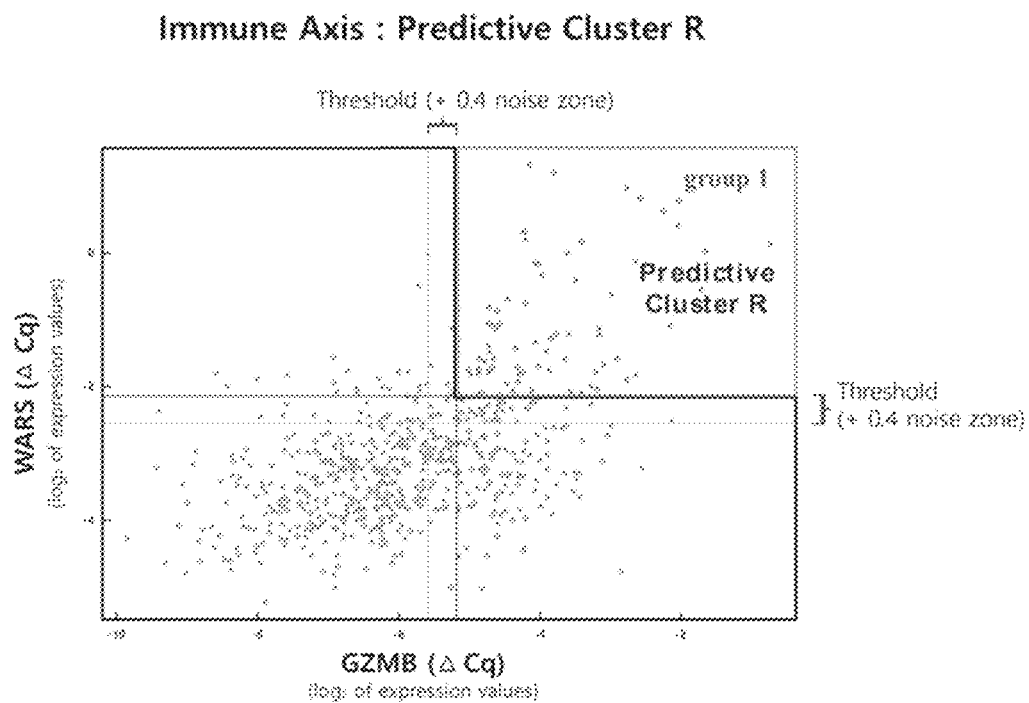
FIG. 4 shows a result illustrating a non-chemotherapy-responder group (Predictive Cluster R) classified from an immune axis in the first tier of a binary signal-based two-tier system of the present invention.

First, in the first tier step, good prognostic (Prognostic Cluster I, the region enclosed by a bold line in FIG. 3) and non-chemotherapy-responder groups (Predictive Cluster R, the region enclosed by a bold line in FIG. 4) were classified by two marker genes (WARS, GZMB) using a Boolean logic gate. Here, the marker genes WARS and GZMB were named immune axis.

Next, in the second tier step, the other gastric cancer patient groups which were not classified in the first tier step were classified in the second tier step, and here, the other two marker genes CDX1 and SFRP4 were used for classification.

Figure 5:
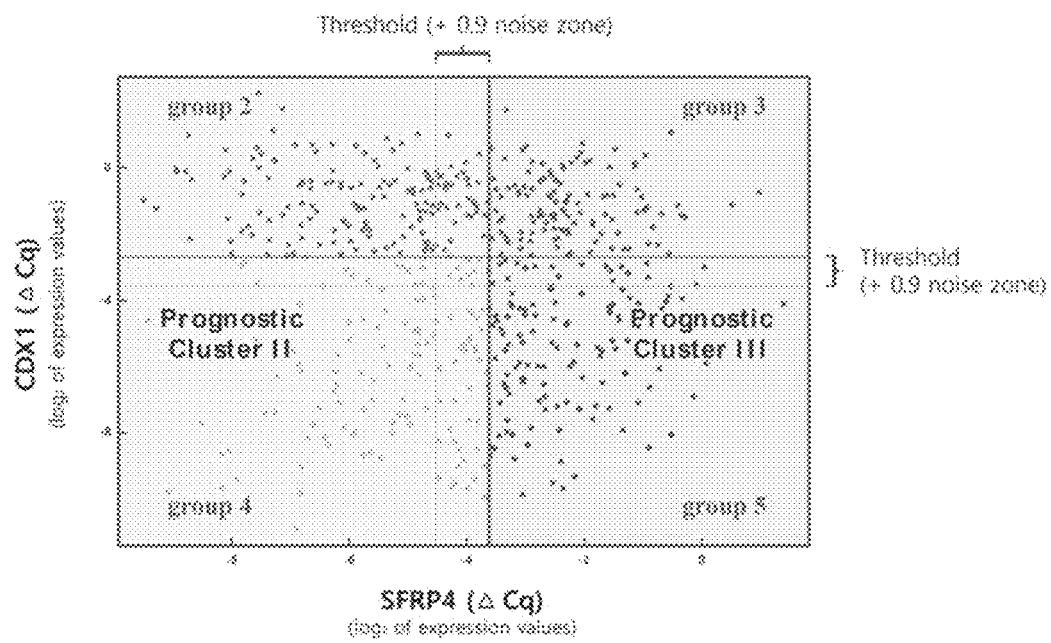
FIG. 5 shows a result illustrating intermediate and bad prognostic groups (Prognostic Cluster II & III) classified from a stem-like axis in the second tier of a binary signal-based two-tier system of the present invention.

Here, in terms of prognostic difference, by a marker gene (SFRP4) representing a stem-like axis, a low expression group was classified as an intermediate prognostic group (Prognostic Cluster II, the left region enclosed by a bold line in FIG. 5), and a high expression group was named a bad prognostic group (Prognostic Cluster III, the right region enclosed by a bold line in FIG. 5).

Figure 6:
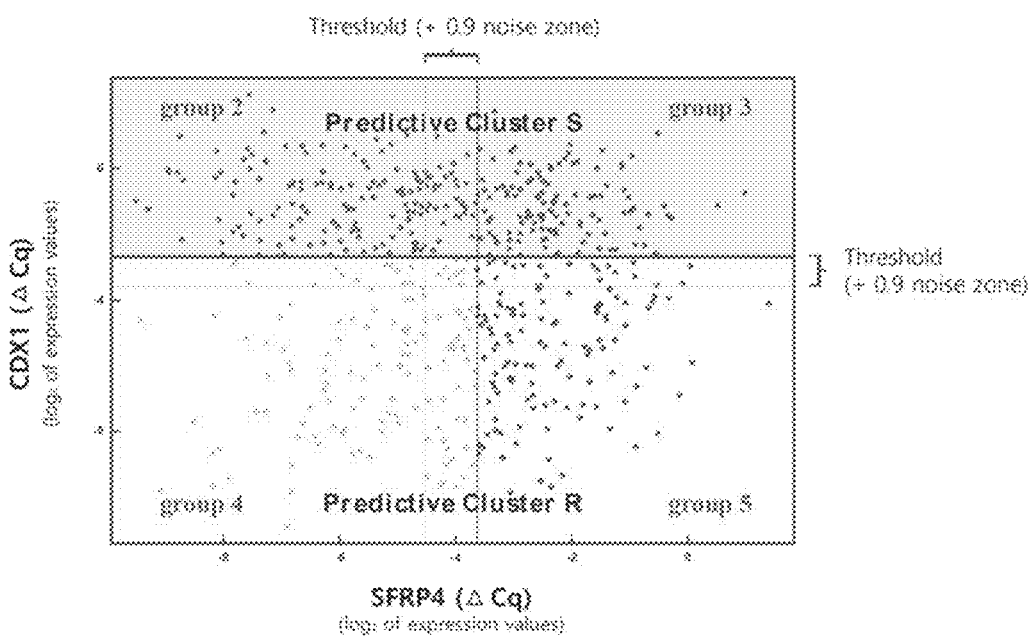
FIG. 6 shows a result illustrating a chemotherapy responder and a non-chemotherapy-responder group (Predictive Cluster S & R), which are classified from an epithelial axis in the second tier of a binary signal-based two-tier system of the present invention.

And then, in terms of chemotherapy responsiveness, by a marker gene (CDX1) representing an epithelial axis, a high expression group was classified as a chemotherapy-responder group (Predictive Cluster S, the upper region enclosed by a bold line in FIG. 6), and a low expression group as well as the groups classified in the first tier step (the region enclosed in a bold line in FIG. 4) were classified as a non-chemotherapy-responder group (Predictive Cluster R, the lower region enclosed by a bold line in FIG. 6).

Figure 7:
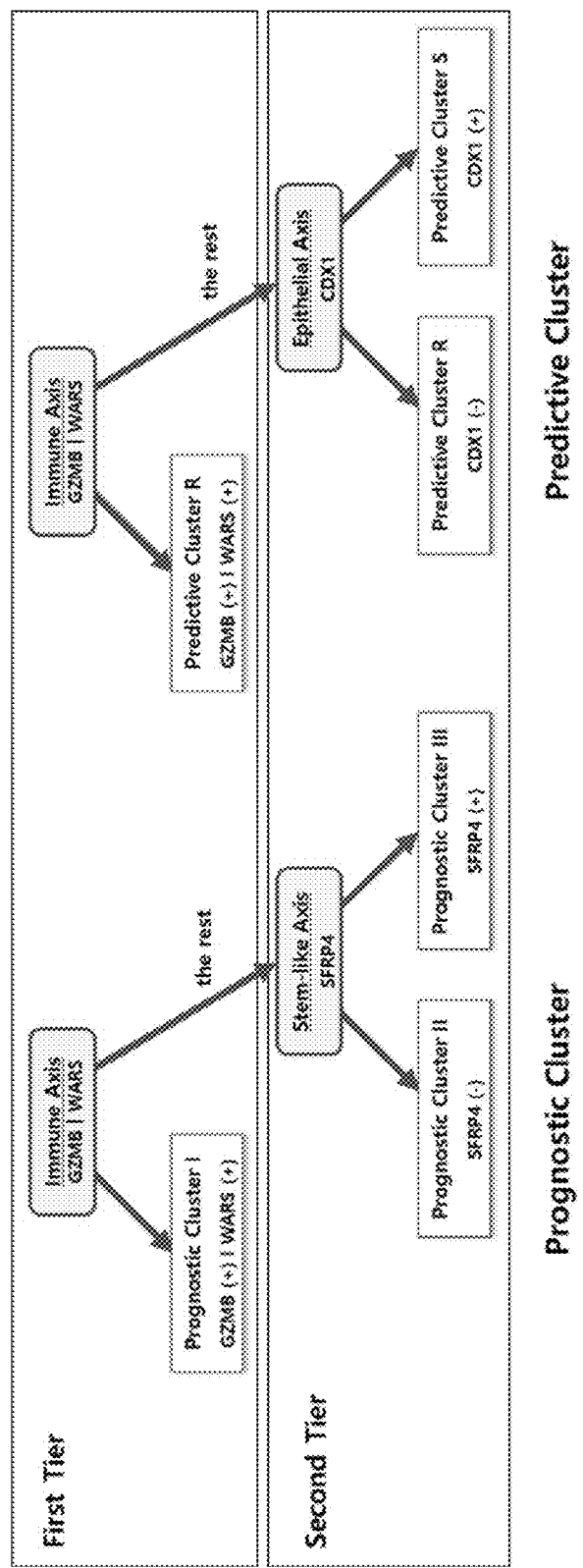
FIG. 7 is a schematic diagram of a binary signal-based two-tier system, which is a classification method for prognostic groups (Prognostic Cluster I, II, III) and chemotherapy responsiveness-related groups (Predictive Cluster R & S) of the present invention.

Such a classification algorithm is illustrated in FIG. 7.

<Example 2> Verification of Algorithm for Predicting Prognosis and Probability of Chemotherapy Responsiveness of Advanced Gastric Cancer Significance of the prognosis and chemotherapy responsiveness according to the prediction algorithm obtained in Example 1 was verified using a Kaplan-Meir curve and COX univariate/multivariate analysis (n=307, three samples were QC failed).

Figure 8:
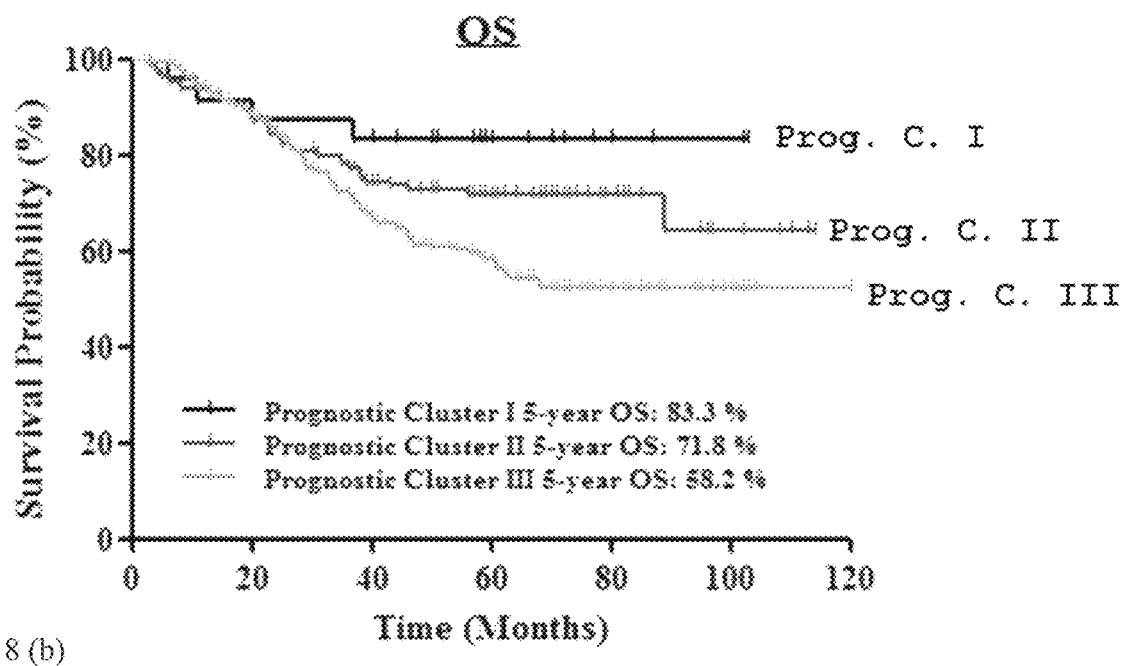
FIGS. 8(a) and 8(b) show (a) Kaplan-Meir curves and (b) log rank test results for overall 5-year survival rates in prognostic groups according to an algorithm that can predict prognosis and chemotherapy responsiveness of advanced gastric cancer of the present invention.

As revealed in the Kaplan-Meir curve of FIG. 8, it can be seen that there was a prognostic difference between three prognostic groups (Prognostic Cluster I, II & III). Overall 5-year survival rates of the three groups were 83.3, 71.8, and 58.2%, respectively, indicating that Prognostic Cluster I had the best prognosis among the three groups, and Prognostic Cluster III had the worst prognosis among these.

TABLE 4

| Variable | Single COX | | Multiple COX | |
| --- | --- | --- | --- | --- |
| Variable | HR (95% CI) | p value | HR (95% CI) | p value |
| Age | | | | |
| <65 vs. >=65 | 1.53 (1.05-2.22) | 0.03 | 1.41 (0.95-2.09) | 0.09 |
| Sex | | | | |
| Female vs. Male | 0.91 (0.60-1.38) | 0.66 | 0.81 (0.53-1.24) | 0.33 |
| T status | | | | |
| T3T4 vs. T1T2 | 1.96 (1.31-2.93) | 0.001 | 2.50 (1.63-3.85) | 3.02e−05 |
| N status | | | | |
| N1N2 vs. N0 | 2.08 (1.01-4.27) | 0.05 | 3.27 (1.54-6.96) | 0.002 |
| Prognostic Cluster | | | | |
| II vs. I | 1.79 (0.63-5.06) | 0.27 | 2.46 (0.86-7.02) | 0.09 |
| III vs. I | 2.93 (1.07-8.02) | 0.04 | 3.32 (1.21-9.11) | 0.02 |
| Chemotherapy | | | | |
| Yes vs. No | 0.90 (0.61-1.32) | 0.58 | 0.79 (0.52-1.19) | 0.26 |

As shown in Table 4, it was identified that the classification of the prognostic groups (Prognostic Clusters) was not only effective in classification of prognosis of the COX univariate/multivariate analysis performed on the prognostic groups of the present invention, but also each prognostic group served as an independent prognosis predictive factor. Particularly, there was a prognostic difference between Prognostic Cluster I and Prognostic Cluster III, and Prognostic Cluster II was determined as a buffer zone.

Figure 9:
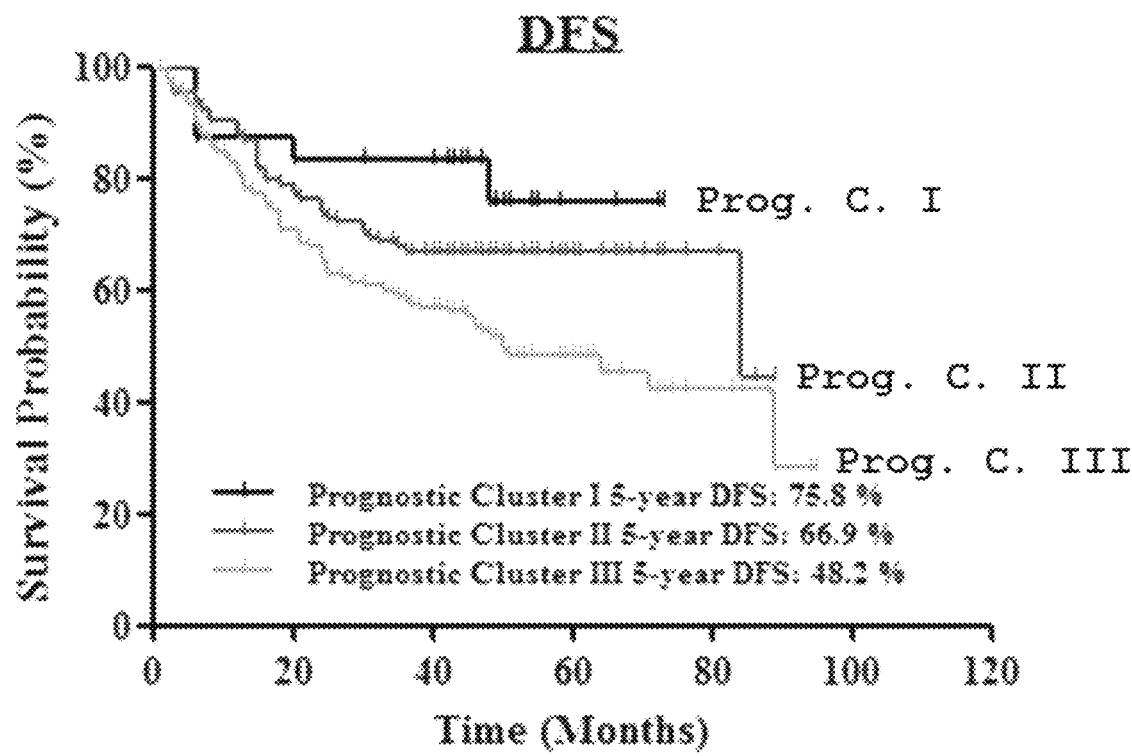
FIGS. 9(a) and 9(b) show (a) Kaplan-Meir curves and (b) log rank test results for 5-year disease-free survival rates in prognostic groups according to the algorithm that can predict prognosis and chemotherapy responsiveness of advanced gastric cancer of the present invention.

The prognosis result was verified in terms of a disease-free survival rate. As shown in the Kaplan-Meir curve of FIG. 9, it can be seen that there was a difference in the disease-free survival rate between the three groups (Prognostic Cluster I, Prognostic Cluster II, Prognostic Cluster III), similar to the result of the overall survival rate. The 5-year disease-free survival rates of the three groups were 75.8%, 66.9% and 48.2%, respectively, indicating that Prognostic Cluster I had the best prognosis among the three groups, and Prognostic Cluster III had the worst prognosis.

In addition, as shown in Table 5, it can be seen that the classification of the prognostic groups (Prognostic Clusters)

was not only effective in classification of prognosis in terms of the disease-free survival rate in the COX univariate/multivariate analysis performed on the prognostic groups of the present invention, but also each prognostic group served as an independent prognosis predictive factor.

TABLE 5

| Variable | Single COX | | Multiple COX | |
|---|---|---|---|---|
| | HR (95% CI) | p value | HR (95% CI) | p value |
| Age | | | | |
| <65 vs. >=65 | 1.42 (1.003-2.02) | 0.05 | 1.40 (0.97-2.02) | 0.07 |
| Sex | | | | |
| Female vs. Male | 0.86 (0.58-1.27) | 0.44 | 0.78 (0.52-1.15) | 0.21 |
| T status | | | | |
| T3T4 vs. T1T2 | 1.96 (1.34-2.85) | 0.0005 | 2.44 (1.62-3.68) | 1.18e−05 |
| N status | | | | |
| N1N2 vs. N0 | 1.76 (0.95-3.27) | 0.073 | 2.67 (1.39-5.15) | 0.003 |
| Prognostic Cluster | | | | |
| II vs. I | 1.73 (0.68-4.40) | 0.25 | 2.35 (0.92-6.04) | 0.08 |
| III vs. I | 2.74 (1.11-6.76) | 0.03 | 3.12 (1.26-7.71) | 0.01 |
| Chemotherapy | | | | |
| Yes vs. No | 1.09 (0.76-1.56) | 0.65 | 0.93 (0.63-1.38) | 0.72 |

Figure 10:
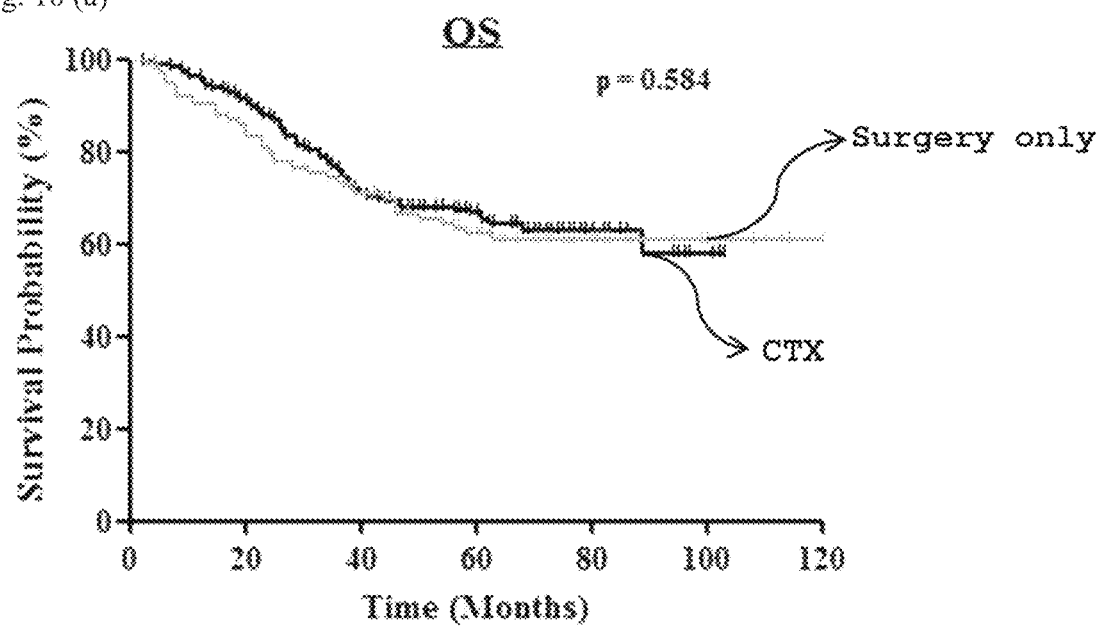
FIGS. 10(a) and 10(b) show (a) p values obtained from the Kaplan-Meier curves and log rank test for overall 5-year survival rates and (b) p values obtained from the Kaplan-Meier curves and log rank test for 5-year disease-free survival rates, in patients with gastric cancer, who received chemotherapy (CTX), did not receive chemotherapy (Surgery only), after being subjected to a gastrectomy.
Figure 10:
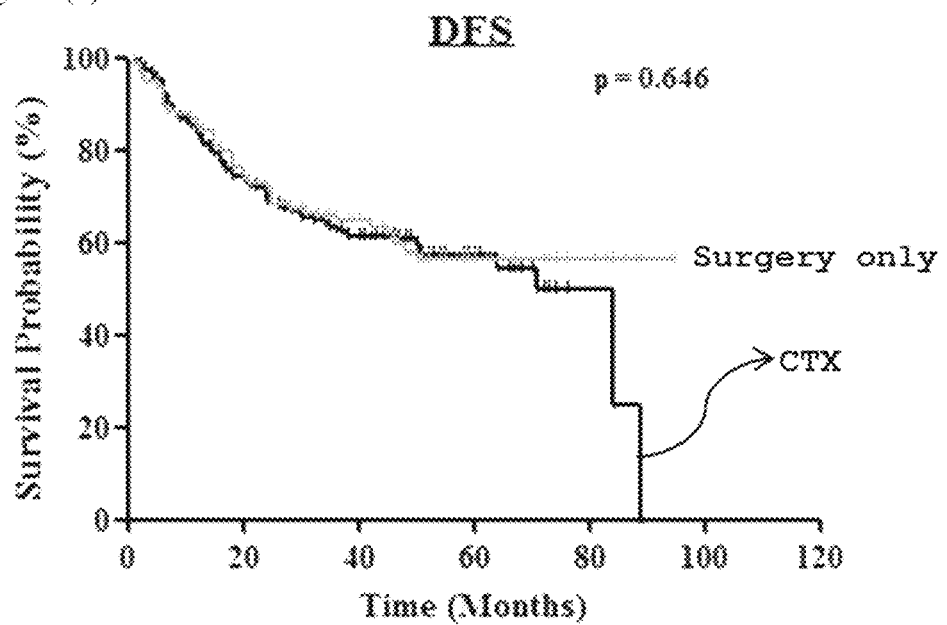

Afterwards, when prognoses were compared for all specimens (n=307) in terms of the overall survival rates of patients who did not receive chemotherapy (Surgery only) and patients who received adjuvant chemotherapy (CTX), after having received a gastrectomy, there was no significant difference between the groups as shown in the Kaplan-Meir curve of FIG. 10. It seems that such a result arises because the specimens were collected as retrospective samples, and determination of whether adjuvant chemotherapy was applied or not applied to a patient was biased. Therefore, data was analyzed by performing COX multivariate analysis using parameters such as sex, age, TNM stage, and chemotherapy treatment in Example 2.

Figure 11:
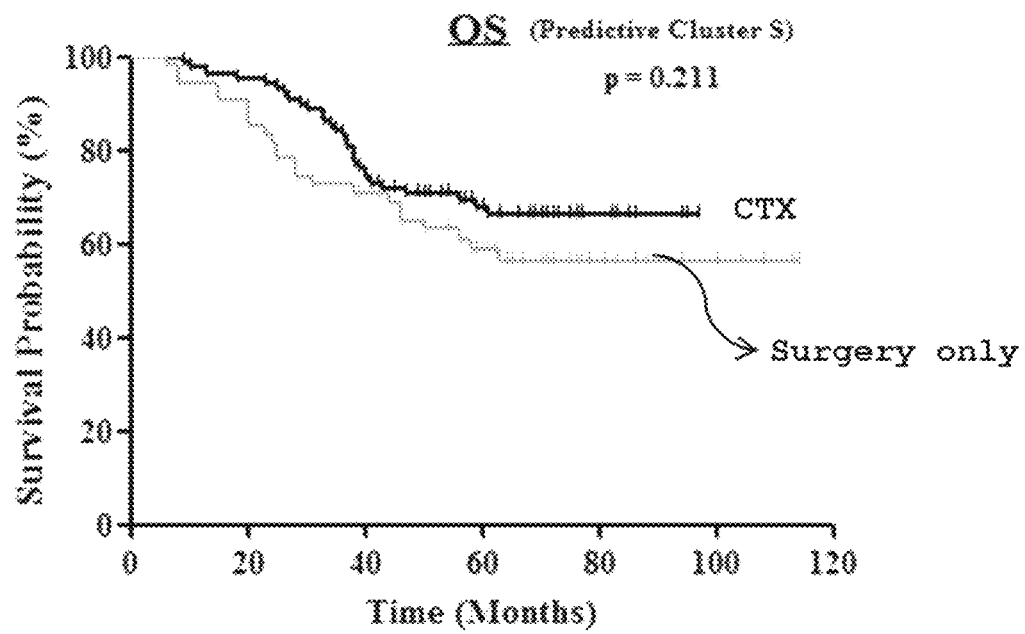
FIG. 11 shows p values obtained from the Kaplan-Meier curves and log rank test for overall 5-year survival rates in patients with gastric cancer, who received chemotherapy (CTX), did not receive chemotherapy (Surgery only), after being subjected to a gastrectomy of a chemotherapy-responder group (Predictive Cluster S), according to the algorithm that can predict the probability of chemotherapy response of advanced gastric cancer of the present invention.

As a result of comparing the prognoses of the patients who received or did not receive chemotherapy in a chemotherapy-responder group (Predictive Cluster S; n=145) according to the present invention, as shown in FIG. 11, there was no significant difference between the group that received chemotherapy and the group that did not receive chemotherapy in the COX univariate analysis, considered to be caused by BIAS in the sample groups. However, according to the COX multivariate analysis using parameters of sex, age and TNM stage, a statistically significant result in which the group that received chemotherapy showed a higher chemotherapy benefit than the group that did not receive chemotherapy is shown (refer to Table 6 and FIG. 11).

TABLE 6

| Variable | Single COX | | Multiple COX | |
|---|---|---|---|---|
| | HR (95% CI) | p value | HR (95% CI) | p value |
| Age | | | | |
| <65 vs. >=65 | 1.56 (0.90-2.71) | 0.11 | 1.40 (0.79-2.50) | 0.25 |
| Sex | | | | |
| Female vs. Male | 0.92 (0.52-1.63) | 0.77 | 0.81 (0.46-1.44) | 0.48 |
| T status | | | | |
| T3T4 vs. T1T2 | 2.13 (1.15-3.93) | 0.02 | 4.01 (2.06-7.81) | 4.53e−05 |
| N status | | | | |
| N1N2 vs. N0 | 2.35 (0.85-6.52) | 0.10 | 5.24 (1.78-15.47) | 0.003 |
| Chemotherapy | | | | |
| Yes vs. No | 0.70 (0.41-1.22) | 0.21 | 0.43 (0.23-0.79) | 0.007 |

Figure 12:
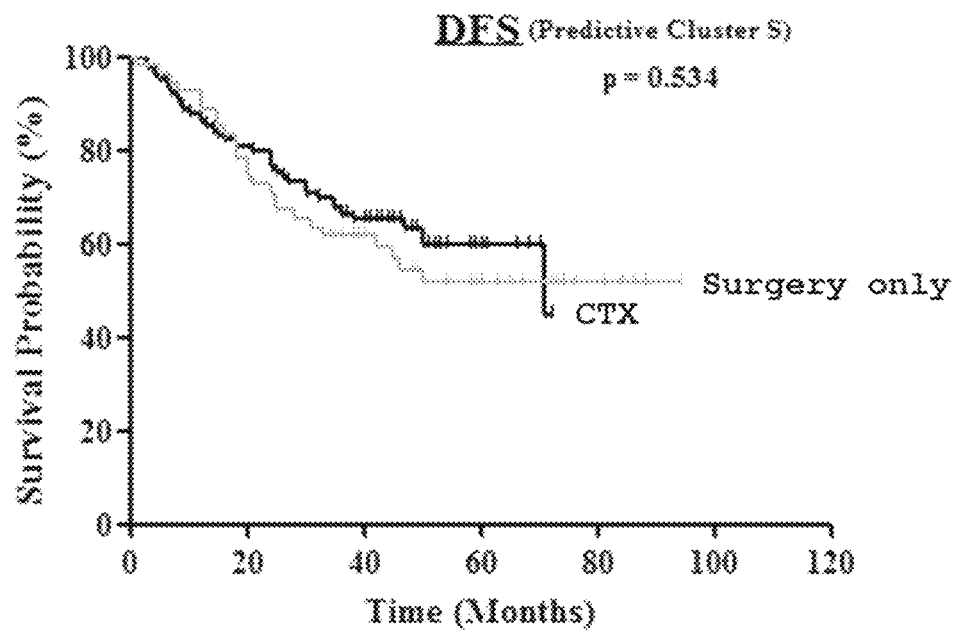
FIG. 12 shows p values obtained from the Kaplan-Meier curves and log rank test for 5-year disease-free survival rates in patients with gastric cancer, who received chemotherapy (CTX), did not receive chemotherapy (Surgery only), after being subjected to a gastrectomy of a chemotherapy-responder group (Predictive Cluster S) according to the algorithm that can predict the probability of chemotherapy response of advanced gastric cancer of the present invention.

As verified in terms of disease-free survival rate, the prognosis showed the same result as that in terms of overall survival rate. In Predictive Cluster S (n=145) according to the present invention, as the prognoses of the patients who received or did not receive chemotherapy was compared in terms of the disease-free survival rate, as shown in FIG. 12, there was no significant difference between the groups that received or did not receive chemotherapy according to COX univariate analysis, whereas according to COX multivariate analysis using parameters such as sex, age and TNM stage, the group that received chemotherapy had a higher chemotherapy benefit than the group that did not receive chemotherapy, which was however marginal. The disease-free survival rate was additionally verified in Example 4 (refer to Table 7 and FIG. 12).

TABLE 7

| Variable | Single COX | | Multiple COX | |
|---|---|---|---|---|
| | HR (95% CI) | p value | HR (95% CI) | p value |
| Age | | | | |
| <65 vs. >=65 | 1.82 (1.09-3.04) | 0.02 | 1.77 (1.04-3.02) | 0.03 |
| Sex | | | | |
| Female vs. Male | 0.78 (0.45-1.34) | 0.36 | 0.68 (0.39-1.18) | 0.17 |
| T status | | | | |
| T3T4 vs. T1T2 | 1.80 (1.03-3.14) | 0.04 | 3.16 (1.69-5.89) | 0.0003 |
| N status | | | | |
| N1N2 vs. N0 | 1.81 (0.78-4.22) | 0.17 | 3.30 (1.31-8.30) | 0.01 |
| Chemotherapy | | | | |
| Yes vs. No | 0.85 (0.50-1.42) | 0.53 | 0.58 (0.32-1.05) | 0.07 |

Figure 13:
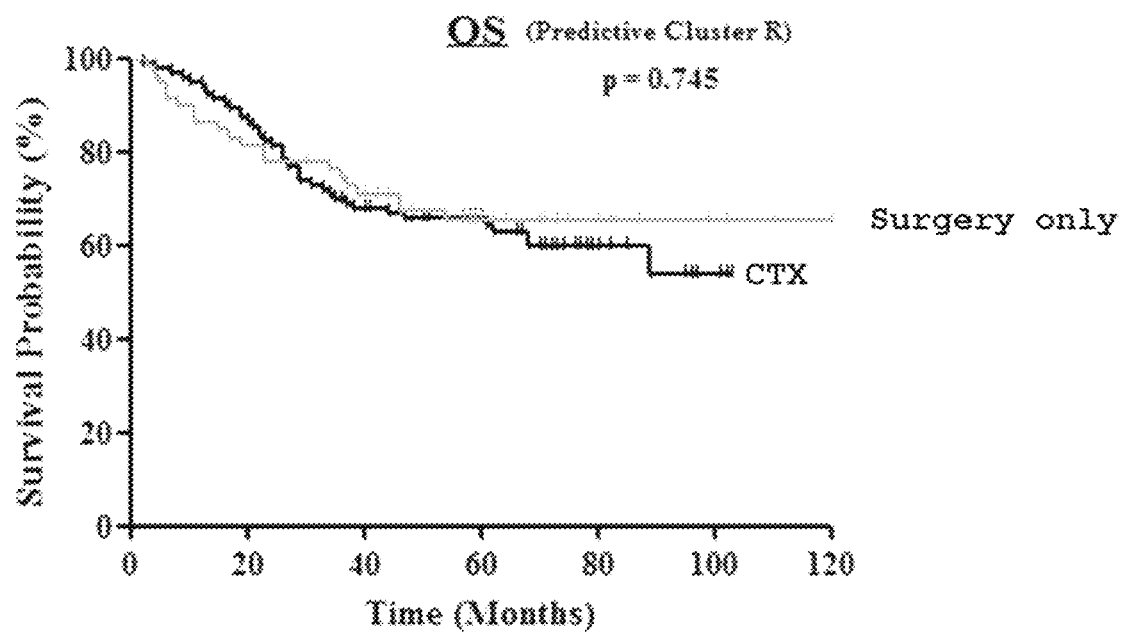
FIG. 13 shows p values obtained from the Kaplan-Meier curves and log rank test for overall 5-year survival rates in patients with gastric cancer, who received chemotherapy (CTX), did not receive chemotherapy (Surgery only), after being subjected to a gastrectomy of a non-chemotherapy-responder group (Predictive Cluster R) according to the algorithm that can predict the probability of chemotherapy response of advanced gastric cancer of the present invention.

Afterwards, in Predictive Cluster R (n=162), as a result of comparing prognoses of patients who received and did not receive chemotherapy in terms of overall survival rate, as shown in FIG. 13, the groups that received and did not receive chemotherapy showed an insignificant difference in survival according to the COX univariate/multivariate analysis (refer to Table 8 and FIG. 13).

Figure 14:
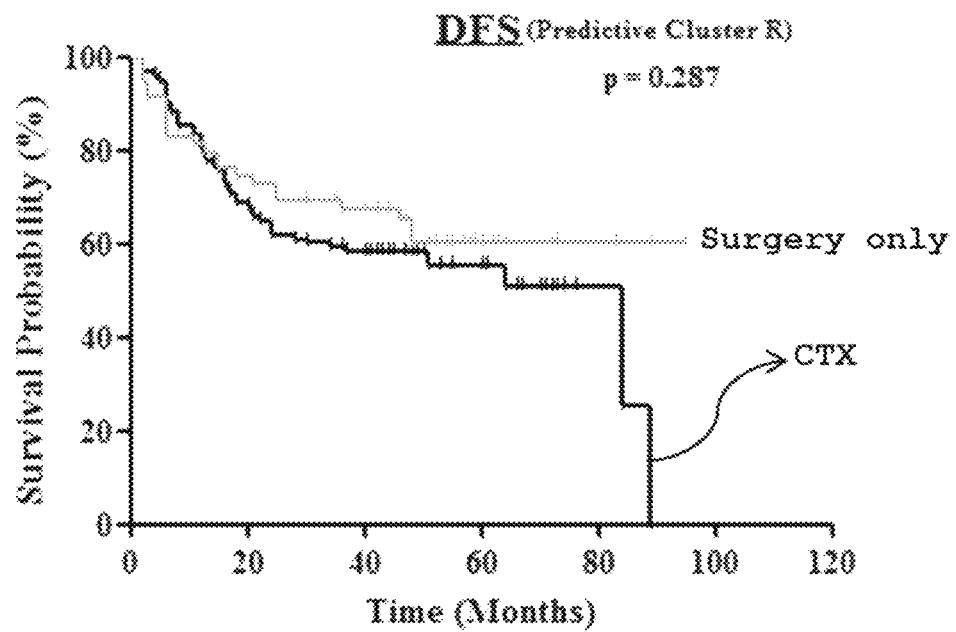
FIG. 14 shows p values obtained from the Kaplan-Meier curves and log rank test for 5-year disease-free survival rates in patients with gastric cancer, who received chemotherapy (CTX), did not receive chemotherapy (Surgery only), after being subjected to a gastrectomy of a non-chemotherapy-responder group (Predictive Cluster R) according to the algorithm that can predict the probability of chemotherapy response of advanced gastric cancer of the present invention.

Finally, as a result of comparing prognoses of patients who received and did not receive chemotherapy in Predictive Cluster R (n=162) in terms of the disease-free survival rate, as shown in FIG. 14, the groups that received and did not receive chemotherapy showed an insignificant difference in survival according to the COX univariate/multivariate analysis (refer to Table 9 and FIG. 14).

TABLE 8

| Variable | Single COX | | Multiple COX | |
|---|---|---|---|---|
| | HR (95% CI) | p value | HR (95% CI) | p value |
| Age | | | | |
| <65 vs. >=65 | 1.47 (0.89-2.45) | 0.13 | 1.48 (0.85-2.57) | 0.17 |
| Sex | | | | |
| Female vs. Male | 0.94 (0.51-1.74) | 0.85 | 0.89 (0.47-1.69) | 0.73 |
| T status | | | | |
| T3T4 vs. T1T2 | 1.83 (1.07-3.14) | 0.03 | 2.09 (1.20-3.62) | 0.0089 |
| N status | | | | |
| N1N2 vs. N0 | 1.80 (0.65-4.95) | 0.26 | 2.25 (0.78-6.45) | 0.13 |
| Chemotherapy | | | | |
| Yes vs. No | 1.09 (0.64-1.87) | 0.75 | 1.20 (0.66-2.19) | 0.55 |

TABLE 9

| Variable | Single COX | | Multiple COX | |
|---|---|---|---|---|
| | HR (95% CI) | p value | HR (95% CI) | p value |
| Age | | | | |
| <65 vs. >=65 | 1.16 (0.72-1.87) | 0.54 | 1.18 (0.71-1.97) | 0.52 |
| Sex | | | | |
| Female vs. Male | 1.02 (0.58-1.79) | 0.94 | 0.97 (0.54-1.74) | 0.93 |
| T status | | | | |
| T3T4 vs. T1T2 | 2.06 (1.23-3.45) | 0.006 | 2.36 (1.40-4.00) | 0.001 |
| N status | | | | |
| N1N2 vs. N0 | 1.77 (0.71-4.40) | 0.22 | 2.36 (0.92-6.10) | 0.08 |
| Chemotherapy | | | | |
| Yes vs. No | 1.31 (0.79-2.18) | 0.30 | 1.28 (0.73-2.26) | 0.38 |

<Example 3> Verification of Interaction Between Classification of Chemotherapy-Responder Groups (Predictive Cluster S & R) and Chemotherapy When comparing the interaction between the chemotherapy responsiveness (Predictive Clusters) and chemotherapy, it was seen that there was no direct interaction between groups attaining advantageous effects from chemotherapy, but it was seen that there was an interaction between chemotherapy responsiveness (Predictive Clusters) and chemotherapy when COX multivariate analysis was performed in terms of retrospective sample bias. This result indicates that, as seen from the COX multivariates analyzed with parameters of age, sex and TNM stage, the benefit of chemotherapy was expected in a chemotherapy-responder group (Predictive Cluster S), but not in a non-chemotherapy-responder group (Predictive Cluster R) (refer to Table 10, Predictive Clusters Multiple COX p-value=0.039).

TABLE 10

| Variable | | Single COX | Multiple COX |
|---|---|---|---|
| | | Chemotherapy interaction p value | |
| Age | <65 vs. >=65 | 0.94 | 0.97 |
| Sex | Female vs. Male | 0.34 | 0.42 |
| T status | T3T4 vs. T1T2 | 0.99 | 0.63 |
| N status | N1N2 vs. N0 | 0.89 | 0.95 |
| Predictive Clusters | R vs. S | 0.27 | 0.039 |

As also verified in terms of the disease-free survival rate, the result was the same as that of the overall survival rate. This indicates that the benefit of chemotherapy was expected in a chemotherapy-responder group (Predictive Cluster S), but not in a non-chemotherapy-responder group (Predictive Cluster R) (refer to Table 11, Predictive Clusters Multiple COX p-value=0.048).

TABLE 11

| Variable | | Single COX | Multiple COX |
|---|---|---|---|
| | | Chemotherapy interaction p value | |
| Age | <65 vs. >=65 | 1.00 | 0.99 |
| Sex | Female vs. Male | 0.29 | 0.28 |
| T status | T3T4 vs. T1T2 | 0.64 | 0.30 |
| N status | N1N2 vs. N0 | 0.79 | 0.59 |
| Predictive Clusters | R vs. S | 0.27 | 0.048 |

As the prognoses of a good prognostic group (Prognostic Cluster I) and a bad prognostic group (Prognostic Cluster III), which were classified according to the algorithm of the present invention, were predicted from the above result, it was seen that there were significant differences in overall 5-year survival rate and disease-free survival rate. As a result of the comparison of the overall 5-year survival rate, the benefits of surgery and chemotherapy are statistically significant in a chemotherapy-responder group (Predictive Cluster S), but not in a non-chemotherapy-responder group (Predictive Cluster R). In addition, this result statistically shows that there was an interaction between the classification of chemotherapy-responder groups and chemotherapy.

<Example 4> Verification of Interactions in XELOX Adjuvant Chemotherapy Benefits Between Prognostic Groups (Prognostic Cluster I, II, III) Using CLASSIC Clinical Trial Sample and Standard Therapy Xeloda+Oxaliplatin (XELOX) Responder Groups (Predictive Cluster R & S)

A CLASSIC (capecitabine and oxaliplatin adjuvant study in stomach cancer) clinical trial is a random Phase 3 international clinical trial performed for each of 37 hospitals in Korea, Japan and China to verify Xeloda+oxaliplatin (XELOX) chemotherapy after surgery (D2 dissection) for stage II and III patients based on AJCC 6th ed. A total of 1037 patients were involved in this trial, and among them, 515 patients were only observed after surgery, and 520 patients were administered Xeloda and oxaliplatin (hereinafter, XELOX), and thus, finally, it was reported that the XELOX-administered group shows a 15% prognosis enhancement effect, compared to the observed group. Therefore, the CLASSIC clinical trial was used as a standard chemotherapy regimen for stage II and III patients.

In the exemplary embodiment, effects on prognosis and chemotherapy responsiveness were verified for 629 samples of the patients participating in the CLASSIC clinical trial using the nProfiler I kit shown in Table 1.

RNA was extracted from the 629 samples as shown in Example 1 and subjected to 1PCR using an nProfiler I Stomach Cancer Assay kit. Quality control was carried out as specified in the nProfiler I kit, and thus four samples were eliminated.

Cq values of a total of 9 genes were measured by the nProfiler I kit, and ΔCq values were calculated according to Equation 1. The calculated ΔCq values was classified as groups as shown in FIG. 7 of Example 1 by applying a reference point for classification according to the predetermined values as shown in Table 3 of Example 1.

Before group classification, prognoses of the group administered XELOX (XELOX) after surgery and the surgery-only group are shown in FIG. 15.

When prognoses were compared between the patient group only observed after surgery (Surgery only) and the patient group administered XELOX, after having received a gastrectomy, it can be seen that there was a significant difference between the groups in all specimens (n=625) as shown in the Kaplan-Meir curve of FIG. 15. Unlike Examples 1, 2 and 3, in <Example 4>, since the specimens were collected from the patient samples of the random Phase 3 clinical trial, it was determined that there was no BIAS in selection of XELOX treatment, and therefore, in <Example 4>, univariate/multivariate analysis was performed. As a result of the analysis, in the COX univariate analysis and the Kaplan Meir plot, there was significant difference in prognoses between the XELOX-administered group (CTX) and the observation-only group (Surgery only), which is the same as the result of the previously published literature (refer to FIG. 15). This result was the same in terms of the disease-free survival rate (refer to FIG. 17).

Significance of prognosis and chemotherapy responsiveness was verified according to the prediction algorithm shown in Example 1 using Kaplan-Meir curves and the COX univariate/multivariate analyses.

As revealed in the Kaplan-Meir curve of FIG. 16, it can be seen that there was a difference in prognoses between the three groups (Prognostic Cluster I, Prognostic Cluster II and Prognostic Cluster III). The overall 5-year survival rates in the three groups were 83.2, 74.8 and 66.0%, respectively, indicating that, among the three groups, Prognostic Cluster I had the best prognosis, and Prognostic Cluster III had the worst prognosis.

In addition, as shown in Table 12, in the COX univariate/multivariate analysis, each subtype was identified as an independent prognosis predictive factor. Particularly, there was a prognostic difference between Prognostic Cluster I and Prognostic Cluster III, and Prognostic Cluster II was determined as a buffer zone.

TABLE 12

| Variable | Single COX | | Multiple COX | |
|---|---|---|---|---|
| | HR (95% CI) | p value | HR (95% CI) | p value |
| Age | | | | |
| <65 vs. >=65 | 1.32 (0.96-1.81) | 0.09 | 1.40 (1.01-1.92) | 0.04 |
| Sex | | | | |
| Female vs. Male | 0.75 (0.53-1.05) | 0.09 | 0.72 (0.51-1.02) | 0.06 |
| T status | | | | |
| T3T4 vs. T1T2 | 1.78 (1.32-2.40) | 0.0001 | 2.01 (1.47-2.74) | 1.25e-05 |
| N status | | | | |
| N1N2 vs. N0 | 1.16 (0.66-2.05) | 0.60 | 1.75 (0.97-3.15) | 0.06 |
| Prognostic Cluster | | | | |
| II vs. I | 1.60 (0.91-2.83) | 0.105 | 1.92 (1.08-3.41) | 0.03 |
| III vs. I | 2.16 (1.22-3.80) | 0.0078 | 2.36 (1.33-4.18) | 0.003 |
| Chemotherapy | | | | |
| Yes vs. No | 0.69 (0.51-0.93) | 0.014 | 0.66 (0.49-0.89) | 0.0067 |

Such a result was verified in terms of a disease-free survival rate as follows. Like the result in terms of the overall survival rate, it can be seen that, in terms of the disease-free survival rate, there was a prognostic difference between the three groups (Prognostic Cluster I, Prognostic Cluster II and Prognostic Cluster III) as shown in the Kaplan-Meir curve of FIG. 18. The 5-year disease-free survival rates in the three groups are 76.9, 65.0 and 55.3%, respectively, indicating that Prognostic Cluster I had the best prognosis and Prognostic Cluster III had the worst prognosis among the three groups.

In addition, as shown in Table 13, as a result of verification in terms of the disease-free survival rate, in the COX univariate/multivariate analysis, each subtype was identified as an independent prognosis predictive factor. Particularly, there was a prognostic difference between Prognostic Cluster I and Prognostic Cluster III, and Prognostic Cluster II was determined as a buffer zone.

TABLE 13

| Variable | Single COX | | Multiple COX | |
|---|---|---|---|---|
| | HR (95% CI) | p value | HR (95% CI) | p value |
| Age | | | | |
| <65 vs. >=65 | 1.24 (0.94-1.64) | 0.12 | 1.34 (1.02-1.77) | 0.04 |
| Sex | | | | |
| Female vs. Male | 0.88 (0.66-1.16) | 0.36 | 0.82 (0.62-1.09) | 0.18 |
| T status | | | | |
| T3T4 vs. T1T2 | 2.01 (1.55-2.60) | 1.19e-07 | 2.16 (1.65-2.84) | 3.02e-08 |
| N status | | | | |
| N1N2 vs. N0 | 0.81 (0.53-1.26) | 0.35 | 1.36 (0.86-2.15) | 0.19 |
| Prognostic Cluster | | | | |
| II vs. I | 1.70 (1.03-2.80) | 0.038 | 2.00 (1.21-3.32) | 0.007 |
| III vs. I | 2.36 (1.44-3.89) | 0.0007 | 2.53 (1.53-4.17) | 0.00028 |
| Chemotherapy | | | | |
| Yes vs. No | 0.65 (0.51-0.85) | 0.0012 | 0.63 (0.49-0.82) | 0.00047 |

Figure 19:
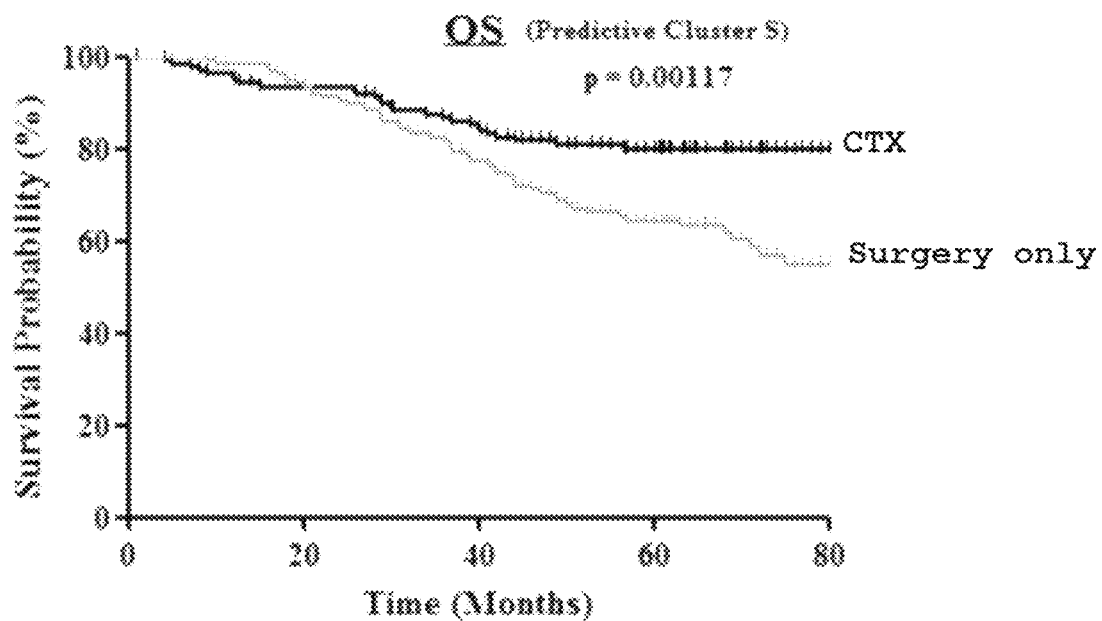
FIG. 19 shows (a) Kaplan-Meir curves and (b) log rank test results for overall 5-year survival rates in a patient group that received Xeloda+oxaliplatin (XELOX) chemotherapy treatment (CTX) and an observation-only group (Surgery only) in a CLASSIC clinical trial sample according to the algorithm that can predict the probability of chemotherapy response of advanced gastric cancer of the present invention.

In Predictive Cluster S (n=281), as prognoses of the patient group that received Xeloda+oxaliplatin (XELOX) chemotherapy treatment (CTX) and the observation-only patient group (Surgery only) are compared in terms of the overall survival rate, as shown in FIG. 19, in the COX univariate analysis, there was a significant difference between the group that received XELOX chemotherapy treatment and the group that did not receive chemotherapy. In the COX multivariate analysis adjusted for sex, age and TNM stage, the group that received XELOX chemotherapy treatment showed a statistically significant result, that is, a good prognosis, which was the same as that in univariate analysis, as compared to the surgery-only group (refer to Table 14 and FIG. 19).

TABLE 14

| Variable | Single COX HR (95% CI) | p value | Multiple COX HR (95% CI) | p value |
|---|---|---|---|---|
| Age | | | | |
| <65 vs. >=65 | 1.03 (0.60-1.76) | 0.92 | 1.02 (0.60-1.75) | 0.94 |
| Sex | | | | |
| Female vs. Male | 0.76 (0.46-1.24) | 0.27 | 0.66 (0.40-1.09) | 0.10 |
| T status | | | | |
| T3T4 vs. T1T2 | 1.96 (1.25-3.05) | 0.003 | 2.27 (1.44-3.60) | 0.0005 |
| N status | | | | |
| N1N2 vs. N0 | 1.46 (0.59-3.62) | 0.41 | 2.43 (0.96-6.18) | 0.061 |
| Chemotherapy | | | | |
| Yes vs. No | 0.47 (0.30-0.75) | 0.002 | 0.46 (0.29-0.74) | 0.0012 |

Figure 20:
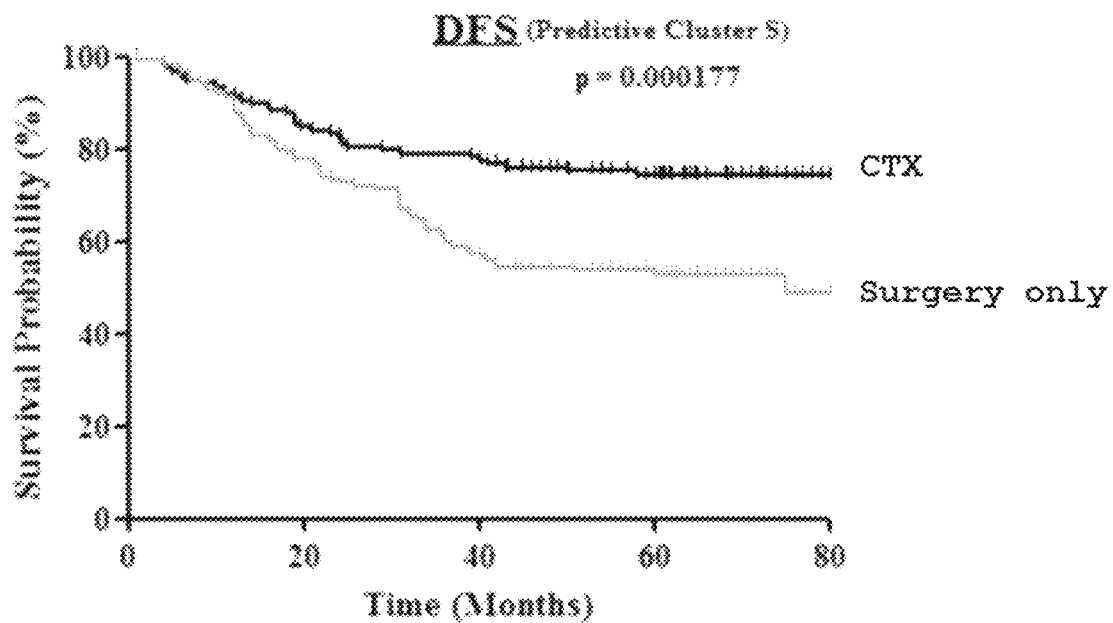
FIG. 20 shows p values obtained from the Kaplan-Meier curves and log rank test for 5-year disease-free survival rates in a patient group that received Xeloda+oxaliplatin (XELOX) chemotherapy treatment (CTX) and an observation-only group (Surgery only) with respect to a CLASSIC clinical trial sample according to the algorithm that can predict the probability of chemotherapy response of advanced gastric cancer of the present invention.

Also, in the verification of the above result in terms of the disease-free survival rate, when, in Predictive Cluster S (n=281), prognoses were compared between the patient group that received XELOX chemotherapy treatment and the observation-only patient group, as shown in FIG. 20, there was a significant difference between the group that received XELOX chemotherapy treatment and the surgery-only group in the COX univariate analysis. In the COX multivariate analysis adjusted for sex, age and TNM stage, the group that received XELOX chemotherapy treatment showed a statistically significant result, that is, a good prognosis, which was the same as that in univariate analysis, as compared to the surgery-only group (refer to Table 15 and FIG. 20).

Figure 21:
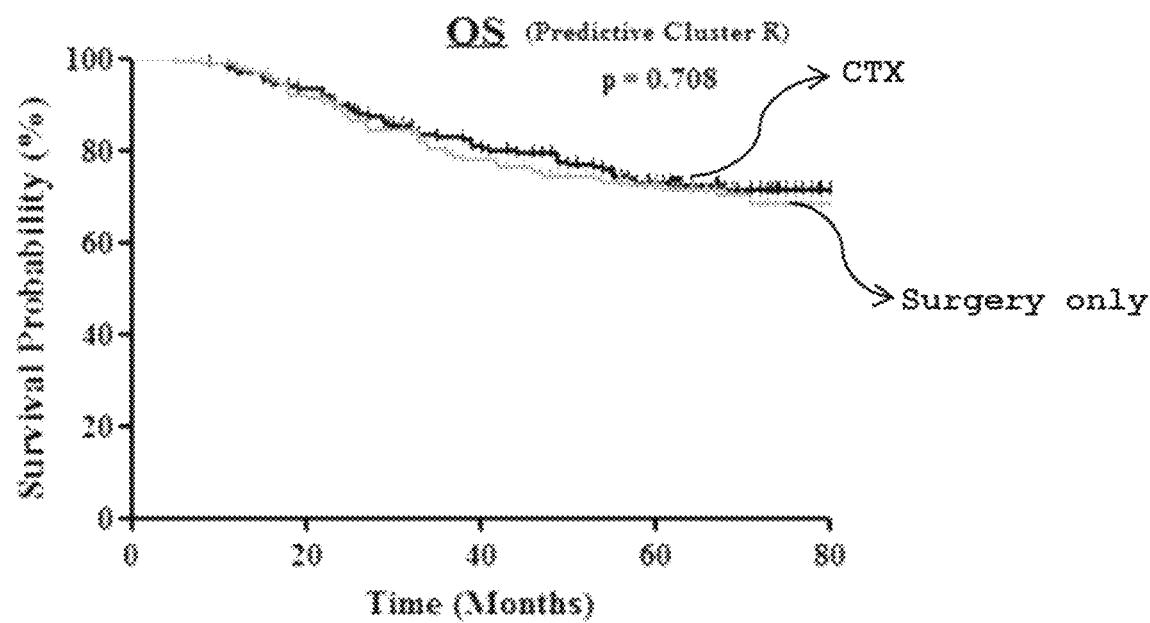
FIG. 21 shows p values obtained from the Kaplan-Meier curves and log rank test for overall 5-year survival rates in a patient group that received Xeloda+oxaliplatin (XELOX) chemotherapy treatment (CTX) and an observation-only group (Surgery only) in a XELOX non-chemotherapy-responder group (Predictive Cluster R) of a CLASSIC clinical trial sample according to the algorithm that can predict the probability of chemotherapy response of advanced gastric cancer of the present invention.

Subsequently, in Predictive Cluster R (n=344), when prognoses were compared between the patient group that received XELOX chemotherapy treatment and the observation-only patient group, as shown in FIG. 21, there was no significant difference in survival between two groups. This result was the same as that in the COX univariate/multivariate analysis (refer to Table 16 and FIG. 21).

TABLE 15

| Variable | Single COX HR (95% CI) | p value | Multiple COX HR (95% CI) | p value |
|---|---|---|---|---|
| Age | | | | |
| <65 vs. >=65 | 1.21 (0.77-1.90) | 0.41 | 1.18 (0.75-1.85) | 0.48 |
| Sex | | | | |
| Female vs. Male | 0.69 (0.44-1.07) | 0.097 | 0.60 (0.38-0.95) | 0.03 |
| T status | | | | |
| T3T4 vs. T1T2 | 2.18 (1.47-3.24) | 0.0001 | 2.59 (1.72-3.88) | 4.66e−06 |
| N status | | | | |
| N1N2 vs. N0 | 1.50 (0.66-3.42) | 0.34 | 2.56 (1.10-5.96) | 0.03 |
| Chemotherapy | | | | |
| Yes vs. No | 0.47 (0.31-0.70) | 0.0002 | 0.45 (0.30-0.68) | 0.0001 |

TABLE 16

| Variable | Single COX HR (95% CI) | p value | Multiple COX HR (95% CI) | p value |
|---|---|---|---|---|
| Age | | | | |
| <65 vs. >=65 | 1.57 (1.04-2.36) | 0.03 | 1.57 (1.04-2.37) | 0.03 |
| Sex | | | | |
| Female vs. Male | 0.73 (0.46-1.18) | 0.20 | 0.75 (0.47-1.20) | 0.23 |
| T status | | | | |
| T3T4 vs. T1T2 | 1.64 (1.10-2.64) | 0.02 | 1.79 (1.18-2.74) | 0.007 |
| N status | | | | |
| N1N2 vs. N0 | 0.99 (0.48-2.04) | 0.98 | 1.24 (0.58-2.66) | 0.58 |
| Chemotherapy | | | | |
| Yes vs. No | 0.93 (0.62-1.38) | 0.71 | 0.90 (0.60-1.36) | 0.63 |

Figure 22:
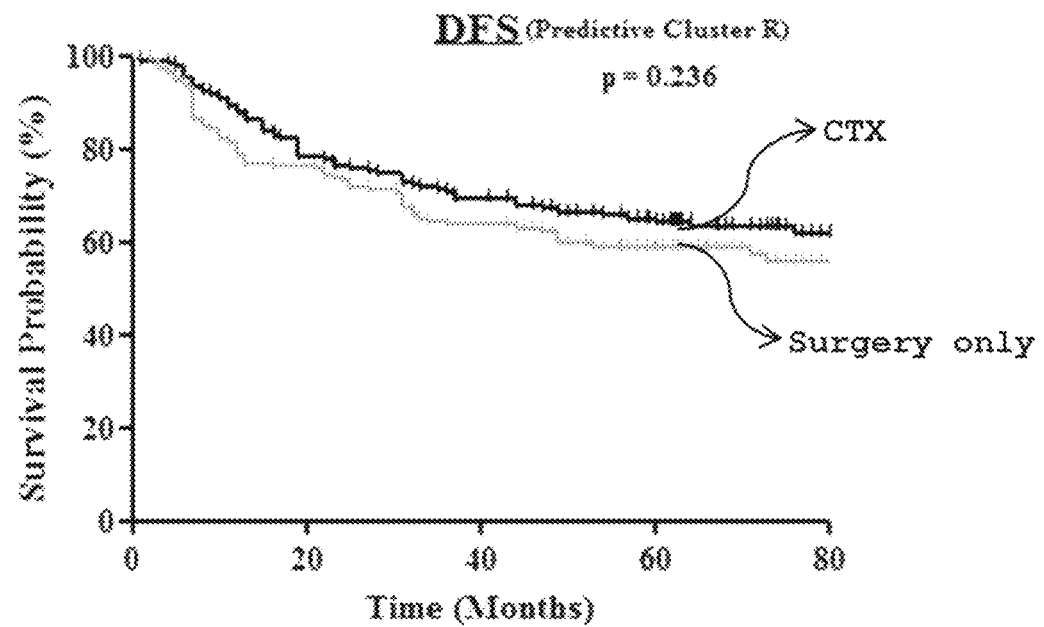
FIG. 22 shows p values obtained from the Kaplan-Meier curves and log rank test for 5-year disease-free survival rates in a patient group that received Xeloda+oxaliplatin (XE-LOX) chemotherapy treatment (CTX) and an observation-only group (Surgery only) in a XELOX non-chemotherapy-responder group (Predictive Cluster R) of a CLASSIC clinical trial sample according to the algorithm that can predict the probability of chemotherapy response of advanced gastric cancer of the present invention.

Subsequently, when the prognoses were verified in terms of the disease-free survival rate, the same result as that of the overall survival rate was observed. In Predictive Cluster R (n=344), when prognoses were compared between the patient group that received XELOX chemotherapy treatment and the observation-only patient group, as shown in FIG. 22, there was no significant difference in survival between two groups. This result was the same as that in the COX univariate/multivariate analysis (refer to Table 17 and FIG. 22).

TABLE 17

| Variable | Single COX HR (95% CI) | p value | Multiple COX HR (95% CI) | p value |
|---|---|---|---|---|
| Age | | | | |
| <65 vs. >=65 | 1.24 (0.87-1.77) | 0.23 | 1.31 (0.92-1.87) | 0.13 |
| Sex | | | | |
| Female vs. Male | 1.04 (0.72-1.50) | 0.84 | 0.99 (0.68-1.44) | 0.97 |
| T status | | | | |
| T3T4 vs. T1T2 | 1.92 (1.36-2.71) | 0.0002 | 1.89 (1.31-2.73) | 0.0006 |
| N status | | | | |
| N1N2 vs. N0 | 0.55 (0.33-0.91) | 0.02 | 0.80 (0.46-1.38) | 0.42 |
| Chemotherapy | | | | |
| Yes vs. No | 0.81 (0.58-1.14) | 0.23 | 0.81 (0.58-1.15) | 0.24 |

Afterwards, when prognosis was verified in terms of the overall survival rate, it was seen that there was a direct interaction between chemotherapy responsiveness (Predictive Cluster) and XELOX chemotherapy treatment (Table 18).

TABLE 18

| Variable | | Single COX Chemotherapy interaction p value | Multiple COX Chemotherapy interaction p value |
|---|---|---|---|
| Age | <65 vs. >=65 | 0.32 | 0.33 |
| Sex | Female vs. Male | 0.87 | 0.88 |
| T status | T3T4 vs. T1T2 | 0.01 | 0.02 |
| N status | N1N2 vs. N0 | 0.82 | 0.97 |
| Predictive Clusters | R vs. S | 0.036 | 0.048 |

When prognosis was verified in terms of the disease-free survival rate, it was seen that there was a direct interaction between the chemotherapy responsiveness (Predictive Cluster) such as overall survival rates and XELOX chemotherapy treatment, as verified in terms of the overall survival rate (Table 19).

This result is obtained by verifying the result of Example 3, and shows that, the advantage of the XELOX chemotherapy occurs in the chemotherapy-responder group (Predictive Cluster S), but does not occur in the non-chemotherapy-responder group (Predictive Cluster R).

As a result of prediction of prognoses in the good prognostic group (Prognostic Cluster I) and the bad prognostic group (Prognostic Cluster III), which are classified by the algorithm of the present invention from the above-described result, it can be seen that there is a significant difference in 5-year survival rate. In addition, the effect of the XELOX chemotherapy after surgery is significantly exhibited in the chemotherapy-responder group (Predictive Cluster S), but there is no therapeutic effect in the non-chemotherapy-responder group (Predictive Cluster R), indicating a significant interaction with the chemotherapy responsiveness and the XELOX treatment.

TABLE 19

| Variable | | Single COX Chemotherapy interaction p value | Multiple COX |
|---|---|---|---|
| Age | <65 vs. >=65 | 0.76 | 0.80 |
| Sex | Female vs. Male | 0.38 | 0.29 |
| T status | T3T4 vs. T1T2 | 0.008 | 0.02 |
| N status | N1N2 vs. N0 | 0.15 | 0.21 |
| Predictive Clusters | R vs. S | 0.043 | 0.066 |

<Example 5> Evaluation of Clinical Performance in Prognostic Groups (Prognostic Cluster I, II and III) Using Rest FFPE Specimens after Surgery for Patients with Stage II and III Advanced Gastric Cancer To verify clinical performance evaluation on the prognosis prediction algorithm of gastric cancer patients obtained in Example 1 (medical device for nProfiler I stomach cancer assay), a ΔCq value of a gene was measured through real time PCR performed on rest FFPE specimens after surgery for patients with stage II and III (based on AJCC $6^{th}$ ed.) gastric cancer, and clinical performance of the algorithm that predicts patient prognosis was tested with a new subject group. Specifically, 1) the prediction performance of the algorithm was evaluated by identifying 5-year survival rates of the two prognostic groups (Prognostic Cluster I, Prognostic Cluster III) deduced from the verification set from Kaplan-Meier curves; 2) the stability of the prognostic difference between groups was evaluated through a comparative test for a prognostic difference between prognostic groups with statistical significance using a log rank test so as to identify that, among the three groups, Prognostic Cluster I is the best prognostic group, and Prognostic Cluster III is the worst prognostic group; and 3) a hazard ratio in a prognostic group was analyzed using a multivariate Cox proportional hazard model so as to identify that the prognostic group is an independent prognostic factor.

For the clinical trial, a total of 684 specimens were used, and in a specimen screening step, 18 specimens were rejected due to insufficient quantity and quality of RNA. Except the screening-rejected 18 specimens, 666 specimens were accepted as specimens for the clinical trial. In a first test and analysis step, 126 specimens out of the total of 666 specimens corresponded to QC failure criteria such that a single time of retesting was performed, resulting in the elimination of 12 specimens among the total of 126 specimens due to the QC failure criteria. As a result, except a total of 30 specimens such as the 18 specimens rejected from the screening and the 12 specimens eliminated due to the re-testing criteria, 654 specimens among the 684 target specimens were selected as an effectiveness evaluation analysis group.

In this clinical trial, there was no evaluation for chemotherapy responsiveness (Predictive Cluster R, S), which was because, since 97.7% of patients among the 654 patient specimens received chemotherapy, there was a lack of patients who did not receive chemotherapy for comparison of a prognostic difference between patients who received chemotherapy and patients who did not receive chemotherapy, which were classified as subgroups by a chemotherapy-responder group (Predictive Cluster R or S).

Figure 23:
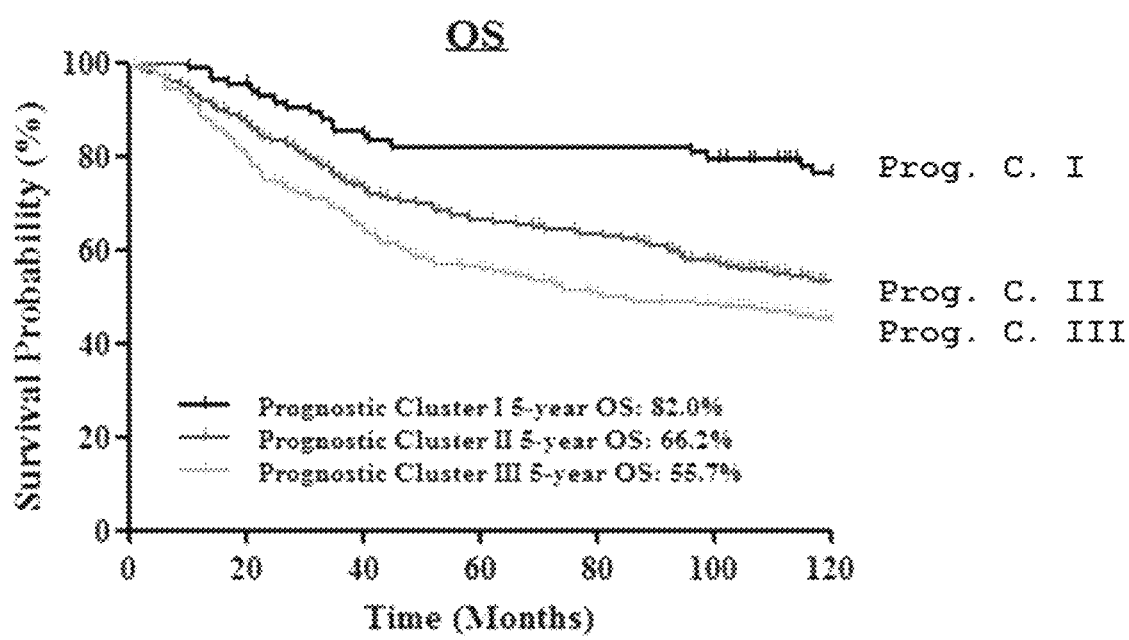
FIG. 23 shows Kaplan-Meier curves for an overall 5-year survival rate in a prognostic group in the evaluation of clinical performance of an algorithm that predicts the prognosis of advanced gastric cancer of the present invention.

First, to measure performance of predicting a 5-year survival rate in prognostic groups, the prognostic groups were classified by applying a ΔCq value per specimen to the algorithm, and then a survival rate per prognostic group was calculated with Kaplan-Meier curves (refer to FIG. 23 and Table 20).

TABLE 20

| Five-year survival of Prognostic clusters | |
|---|---|
| Prognostic Cluster | Overall survival Survival rate (95% CI) |
| Prognostic Cluster I | 0.8198 (0.7412-0.9067) |
| Prognostic Cluster II | 0.6618 (0.6058-0.7230) |
| Prognostic Cluster III | 0.5574 (0.5052-0.6149) |

In addition, as a result of checking overlapping between the 95% confidence intervals of two prognostic groups such as prognostic group I and prognostic group III, it was confirmed that there was no overlapping as shown in Table 21 below.

TABLE 21

| Classification | 95% confidence interval of 654 samples | Test of overlapping 95% confidence interval between Prognostic Clusters I and III |
|---|---|---|
| 95% confidence interval in Prognostic Cluster I | 74.12%~90.67% | The confidence intervals of Prognostic Cluster I and Prognostic Cluster III are not overlapped |
| 95% confidence interval in Prognostic Cluster III | 50.52%~61/49% | |

To confirm stability in the difference between prognostic groups, prognostic groups I, II and III were subjected to a log rank test to identify a statistically significant difference, and for statistical calculation, a p value was calculated by calculating a chi square with 2 degrees of freedom. If there was no difference in the effect of comparing prognostic groups, the occurrence of an event (death) in all sections has to happen in a frequency proportional to the number of subjects to be observed (0) in the three prognostic groups in each section. In the log rank test, the entire cluster that summarizes the three prognostic groups was arranged in order of observation time, and from this, the censored entry was eliminated to leave only a section in which the event (death) occurred. In addition, the expected frequency (E) of death for each prognostic group was calculated. Since the interaction between the total observation frequency (O) and expected frequency (E) with respect to death for each prognostic group showed a chi-squared distribution with two degrees of freedom, if the value ($X^2$) was larger than 5.99 (p value<0.05), it was considered that the three prognostic groups show a significant difference. The null hypothesis in the log rank test was as follows:

$H_0$: no difference between Prognostic Cluster I, II and III

Method for Calculating Expected Frequency (Expected Death Rate)

$$E1j = \frac{Oj \times N1j}{Nj}$$

($E_{1j}$: Expected mortality of $j^{th}$ variable in Group 1; Oj: Observed mortality of $j^{th}$ variables in all groups; $N_{1j}$: Number of observation subjects of $j^{th}$ variable in Group 1; Nj: Number of observation subjects of $j^{th}$ variables in all groups)

Statistics of log-rank test between two or more groups: Chi-square $X^2 = Z(\Sigma^{-1})Z^t$ ($\Sigma$: variance-covariance matrix, Z: k−1 statistic vector)

When the p values with respect to the statistics of the log rank test are smaller than 0.05, it was interpreted that there is a prognostic difference between the prognostic groups, and on the contrary, when the p value with respect to the statistic was larger than 0.05, it was interpreted that there is no difference in prognosis between the prognostic groups.

As a result, when the chi square ($X^2$) with 2 degrees of freedom was calculated as 24.7 (p value=4.39e−06), a statistically significant difference was indicated (refer to Table 22). Therefore, it can be seen that there was a prognostic difference between the three groups (Prognostic Cluster I, II and III).

TABLE 22

| | N | Observed | Expected | (O-E)^2/E | (O-E)^2/V |
|---|---|---|---|---|---|
| cluster. all = 1 | 84 | 24 | 52.3 | 15.312 | 18.41 |
| cluster. all = 2 | 253 | 122 | 129.6 | 0.446 | 0.74 |
| cluster. all = 3 | 317 | 185 | 149.1 | 8.645 | 15.87 | chisq = 24.7 on 2 degrees of freedom,
p = 4.39e−06

To investigate where the difference between the three prognostic groups originates, as a result of performing a post-hoc test having chi-squared distribution with two degrees of freedom using a log rank test, it can be seen that there was a difference in prognosis by calculating all significant p values. That is, since the difference between the three prognostic groups was apparent, it was judged that this result satisfies the [the stability in the difference between prognostic groups].

TABLE 23

| Prognostic Cluster for analysis | Number of samples to be observed | Chi-square ($X^2$) | P value |
|---|---|---|---|
| Prognostic Cluster I vs. Prognostic Cluster II | 337 | 11.5 | 0.000691 |
| Prognostic Cluster vs. Prognostic Cluster III | 401 | 22.6 | 1.96e−06 |
| Prognostic Cluster II vs. Prognostic Cluster III | 570 | 5.8 | 0.016 |

To confirm a hazard degree and independence of the prognostic groups, the influence of other risk factors (age, sex, TNM stage, and chemotherapy) of gastric cancer was corrected to evaluate whether there was a difference in survival rate according to a risk factor, that is, a prognostic group itself, through hazard ratio analysis. Using a Cox proportional hazard model analysis method, a multivariate analysis using a pre-existing prognosis factor as a covariate was performed to investigate whether the prognostic group according to the algorithm was an independent prognostic factor which affected the prognosis of gastric cancer.

The null analysis in the Cox proportional hazard model was as follows:

$H_0$: $\beta_j=0$ means that two persons having different risk factors are proportionally related regardless of time (t).

$$h(t)=h_0(t)\exp(\beta_1\chi_1+ \ldots +\beta_k\chi_k)$$

[$\chi_1, \ldots, \chi_k$: independent variables (risk factors), $h_0(t)$: baseline hazard at time t, that is, indicating a hazard to a person with "0" value for all independent variables]

$$\text{Hazard ratio}\frac{h(t)}{h_0(t)} = \exp(\beta_j)$$

Statistics and P Value Calculation $Z=\hat{\beta}_j/se(\hat{\beta}_j)$

When $Z<Z_{\alpha/2}$ or $Z<Z_{1-\alpha/2}$, $H_0$ is rejected, and when $Z_{\alpha/2} \leq Z \leq Z_{1-\alpha/2}$, $H_0$ is adopted.

p value=$2\times[1-\Phi(Z)]$ if $Z \geq 0$,
$2\times\Phi(Z)$ if $Z<0$

Then, among 654 samples selected as an effectiveness evaluation analysis group, 22 samples which were uncertain as to whether chemotherapy was received were eliminated from the analysis, and the remaining 632 samples were analyzed using a multivariate Cox proportional hazard model to calculate a hazard ratio, and a 95% confidence interval and a p value therefor.

As an analysis result of a multivariate Cox proportional hazard model, when the hazard ratio between two prognosis clusters (Prognostic Cluster I vs. Prognostic Cluster III) was statistically significant (p value<0.05), it was interpreted that the prognostic group according to the algorithm was an independent prognostic factor.

TABLE 24

Result of multivariate COX's proportional hazard regression model analysis

| | Hazard Ratio with 95% CI | p value |
|---|---|---|
| Age | 1.0200 (1.0098-1.0300) | 0.000112 |
| Sex | | |
| Male | 1 | |
| Female | 1.1223 (0.8893-1.4160) | 0.331330 |
| Chemotherapy | | |
| No | 1 | |
| Yes | 0.7531 (0.3715-1.5260) | 0.431482 |
| TNM stage | | |
| Stage II | 1 | |
| Stage III | 2.0315 (1.5882-2.5990) | 1.67e−08 |
| Prognostic Cluster | | |
| Prognostic Cluster I | 1 | |
| Prognostic Cluster II | 2.0439 (1.3155-3.1760) | 0.001475 |
| Prognostic Cluster III | 2.5765 (1.6810-3.9490) | 1.40e−05 |

As a result of analysis using the Cox proportional hazard model, it was shown that, as risk factors (independent variables) affecting prognosis gastric cancer, the age (p value=0.000112), the TNM stage (p value=1.67e−08) and the prognostic group were statistically significant.

In the case of the prognostic group (Prognostic Cluster) which is an evaluation variable for the clinical trial, a hazard ratio of Prognostic Clusters II and III was calculated using Prognostic Cluster I as the reference of a corresponding independent variable. Therefore, in diagnosis, compared to Prognostic Cluster I, Prognostic Cluster II (p value=0.001475) was 2.04-fold more hazardous, and Prognostic Cluster III (p value=1.40e−05) was 2.58-fold more hazardous, which were statistically significant.

Therefore, even though the Cox proportional hazard model was adjusted with the risk factors (age, sex, TNM stage, and chemotherapy), it was seen that the classification of Prognostic Clusters according to the algorithm is an independent prognostic factor in gastric cancer.

As a result of evaluating the safety of the clinical trial, during the corresponding period, a tester stored and handled a specimen according to laboratory biological safety guidelines. According to observation during a period of the clinical trial, there was no safety issue related to side effects such as abnormal cases and infections from specimens to a tester handling the specimen.

An evaluation result for clinical effectiveness of prognosis was verified using applying the prediction algorithm obtained in Example 1 through the clinical trial and a threshold value of the algorithm. The 5-year survival rates in Prognostic Cluster I and Prognostic Cluster III as effectiveness evaluation variables were confirmed as 81.98% (95% CI, 74.12 to 90.67%) and 55.74 (95% CI, 50.52 to 61.49%), respectively, met the evaluation criteria set in the clinical trial plan, and it was confirmed that 95% CI of the 5-year survival rates in prognostic group I and prognostic group III did not overlap with each other.

In addition, according to a log rank test performed to evaluate whether there was a prognostic difference between the three classified prognostic groups, it was confirmed that there was a significant difference between the three groups. In addition, according to the post-hoc analysis, significant p values were calculated from all of the three groups, indicating that there was a prognostic difference between the groups. That is, since, between the three prognostic groups, the difference between the prognostic groups was clear, the result satisfies the [stability in the difference between prognostic groups].

Finally, as a hazard ratio was estimated by performing multivariate Cox proportional hazard model analysis using age, sex, chemotherapy, stage, etc. as covariates, compared to Prognostic Cluster I, Prognostic Cluster II (p value=0.001475) was 2.04-fold more hazardous, and compared to Prognostic Cluster I, Prognostic Cluster III (p value=1.40e−05) was 2.58-fold more hazardous, which were statistically significant. That is, it was confirmed that Prognostic Cluster I had the best prognosis, and Prognostic Cluster III had the worst prognosis. That is, even though the Cox proportional hazard model was adjusted with risk factors (e.g., age, sex, TNM stage and chemotherapy), it can be seen that the classification of a prognostic cluster according to the algorithm was an independent prognostic factor in gastric cancer.

Consequently, as shown in the evaluation result for the clinical trial, the prognosis prediction algorithm for a gastric cancer patient, which was obtained from Example 1, and clinical performance of a medical device for an nProfiler I stomach cancer assay were considered to be successfully evaluated.

The present invention can be used as supplementary information to determine a method for treating a gastric cancer patient.

What is claimed is:

1. A method for predicting prognosis of stage II or III gastric cancer, the method comprising:
   a) determining a reference final threshold value per WARS, GZMB, CDX1 and SFRP4, respectively and three prognostic groups based on the reference final threshold value to predict prognosis after surgery of stage II or III gastric cancer, comprising
      i) calculating a ΔCq value per WARS, GZMB, CDX1 and SFRP4, respectively according to mRNA expression levels of WARS, GZMB, CDX1 and SFRP4 as the prognosis or chemotherapy responsiveness-related marker gene group, and mRNA expression levels of ACTB, ATP5E, GPX1, UBB and HPRT1 as the reference gene group measured from a plurality of cancer tissue samples of stage II or stage III gastric cancer patients for which statistical calculations are possible, according to Equation 1 below,
      ii) obtaining the reference final threshold value per WARS, GZMB, CDX1 and SFRP4, respectively by calculating an adaptive regression value per gene using the ΔCq values and adding a correction value per gene to the adaptive regression value,
      wherein the adaptive regression values of WARS, GZMB, CDX1 and SFRP4 are −2.54, −5.58, −3.59 and −4.53, respectively, and the correction values thereof are +0.4, +0.4, +0.9 and +0.9, respectively,
      wherein the reference final threshold value per WARS, GZMB, CDX1 and SFRP4 is −2.14, −5.18, −2.69 and −3.63, respectively; and
      iii) classifying the plurality of cancer tissue samples into three prognostic groups based on the reference final threshold values of WARS, GZMB, CDX1 and SFRP4 by using a binary signal-based two-tier system,
      wherein among the plurality of cancer tissue samples, those with the ΔCq values of GZMB and WARS higher than the reference final threshold values of GZMB and WARS in the plurality of cancer tissue samples are classified as a good prognostic group (Prognostic Cluster I), for the remaining samples with ΔCq values of two or any one of GZMB and WARS lower than the reference final threshold values of GZMB and WARS, based on the ΔCq value of SFRP4, those with the ΔCq value of SFRP4 lower than the reference final threshold value of SFRP4 are classified as an intermediate prognostic group (Prognostic Cluster II), and those with the ΔCq value of SFRP4 higher than the reference final threshold value of SFRP4 are classified as a bad prognostic group (Prognostic Cluster III);

b) calculating a ΔCq value per WARS, GZMB, CDX1 and SFRP4, respectively according to mRNA expression levels of WARS, GZMB, CDX1 and SFRP4 as the prognosis or chemotherapy responsiveness-related marker gene group, and mRNA expression levels of ACTB, ATP5E, GPX1, UBB and HPRT1 as the reference gene group measured from a biological sample of stage II or III gastric cancer patient, according to Equation 1 below; and c) predicting prognosis of the biological sample by comparing each of the ΔCq values of WARS, GZMB, CDX1 and SFRP4 calculated in b) step with the reference final threshold value per WARS, GZMB, CDX1 and SFRP4, respectively determined in a) step, wherein the mRNA expression levels of genes mentioned in a) step and b) step are measured by using a set of primers set forth in SEQ ID NOs: 1 to 18; and probes set forth in SEQ ID NOs: 19 to 27, wherein [Equation 1] is as follows:

$$\Delta Cq = (Cq \text{ value of reference gene group}) - (Cq \text{ value of prognosis or chemotherapy responsiveness-related marker gene})$$

wherein the Cq value of the reference gene group refers to an average Cq value of reference genes consisting of ACTB, ATP5E, GPX1, UBB and HPRT1.

2. The method according to claim 1, wherein the biological sample is selected from the group consisting of fresh tumor tissue, fresh frozen tumor tissue, paraffin-embedded tumor tissue, a fine needle aspiration fluid, ascites, a tube washing solution, and a pleural fluid.

3. The method according to claim 1, wherein the measurement of mRNA expression levels of the prognosis or chemotherapy responsiveness-related marker gene group and the reference gene group is performed by RT-PCR, competitive RT-PCR or real time RT-PCR.

4. A method for predicting chemotherapy responsiveness of stage II or III gastric cancer, the method comprising:

a) determining a reference final threshold value per WARS, GZMB, CDX1 and SFRP4, respectively and three prognostic groups based on the reference final threshold value to predict chemotherapy responsiveness after surgery of stage II or III gastric cancer, comprising i) calculating a ΔCq value per WARS, GZMB, CDX1 and SFRP4, respectively according to mRNA expression levels of WARS, GZMB, CDX1 and SFRP4 as the prognosis or chemotherapy responsiveness-related marker gene group, and mRNA expression levels of ACTB, ATP5E, GPX1, UBB and HPRT1 as the reference gene group measured from a plurality of cancer tissue samples of stage II or stage III gastric cancer patients for which statistical calculations are possible, according to Equation 1 below, ii) obtaining the reference final threshold value per WARS, GZMB, CDX1 and SFRP4, respectively by calculating an adaptive regression value per gene using the ΔCq values and adding a correction value per gene to the adaptive regression value, wherein the adaptive regression values of WARS, GZMB, CDX1 and SFRP4 are −2.54, −5.58, −3.59 and −4.53, respectively, and the correction values thereof are +0.4, +0.4, +0.9 and +0.9, respectively, wherein the reference final threshold value per WARS, GZMB, CDX1 and SFRP4 is −2.14, −5.18, −2.69 and −3.63, respectively; and iii) classifying the plurality of cancer tissue samples into two predictive clusters based on the reference final threshold values of WARS, GZMB, CDX1 and SFRP4 by using a binary signal-based two-tier system, wherein among the plurality of cancer tissue samples, those with the ΔCq values of GZMB and WARS higher than the reference final threshold values of GZMB and WARS in the plurality of cancer tissue samples are classified as a non-chemotherapy-responder group (Predictive Cluster R), for the remaining samples with ΔCq values of two or any one of GZMB and WARS lower than the reference final threshold values of GZMB and WARS, based on the ΔCq value of CDX1, those with the ΔCq value of CDX1 lower than the reference final threshold value of SFRP4 are classified as the non-chemotherapy-responder group (Predictive Cluster R), and those with the ΔCq value of CDX1 higher than the reference final threshold value of SFRP4 are classified as a chemotherapy-responder group (Predictive Cluster S);

b) calculating a ΔCq value per WARS, GZMB, CDX1 and SFRP4, respectively according to mRNA expression levels of WARS, GZMB, CDX1 and SFRP4 as the prognosis or chemotherapy responsiveness-related marker gene group, and mRNA expression levels of ACTB, ATP5E, GPX1, UBB and HPRT1 as the reference gene group measured from a biological sample of stage II or III gastric cancer patient, according to Equation 1 below; and c) predicting chemotherapy responsiveness of the biological sample by comparing each of the ΔCq values of WARS, GZMB, CDX1 and SFRP4 calculated in b) step with the reference final threshold value per WARS, GZMB, CDX1 and SFRP4, respectively determined in a) step, and wherein the m RNA expression levels of genes mentioned in a) step and b) step are measured by using a set of primers set forth in SEQ ID NOs: 1 to 18; and probes set forth in SEQ ID NOs: 19 to 27, wherein [Equation 1] is as follows:

$$\Delta Cq = (Cq \text{ value of reference gene group}) - (Cq \text{ value of prognosis or chemotherapy responsiveness-related marker gene})$$

wherein the Cq value of the reference gene group refers to an average Cq value of reference genes consisting of ACTB, ATP5E, GPX1, UBB and HPRT1.

5. The method according to claim 4, wherein the biological sample is selected from the group consisting of fresh tumor tissue, fresh frozen tumor tissue, paraffin-embedded tumor tissue, a fine needle aspiration fluid, ascites, a tube washing solution, and a pleural fluid.

6. The method according to claim 4, wherein the measurement of mRNA expression levels of the prognosis or chemotherapy responsiveness-related marker gene group and the reference gene group is performed by RT-PCR, competitive RT-PCR or real time RT-PCR.

\* \* \* \* \*

SEQUENCE LISTING

```
<160> NUMBER OF SEQ ID NOS: 27

<210> SEQ ID NO 1
<211> LENGTH: 22
<212> TYPE: DNA
<213> ORGANISM: Artificial Sequence
<220> FEATURE:
<223> OTHER INFORMATION: SFRP4 forward primer

<400> SEQUENCE: 1
ggagacttcc gacttcctta ca                                              22

<210> SEQ ID NO 2
<211> LENGTH: 20
<212> TYPE: DNA
<213> ORGANISM: Artificial Sequence
<220> FEATURE:
<223> OTHER INFORMATION: SFRP4 reverse primer

<400> SEQUENCE: 2
tggccttaca taggctgtcc                                                 20

<210> SEQ ID NO 3
<211> LENGTH: 20
<212> TYPE: DNA
<213> ORGANISM: Artificial Sequence
<220> FEATURE:
<223> OTHER INFORMATION: GZMB forward primer

<400> SEQUENCE: 3
```
cggtggcttc ctgatacaag                                                20

<210> SEQ ID NO 4
<211> LENGTH: 20
<212> TYPE: DNA
<213> ORGANISM: Artificial Sequence
<220> FEATURE:
<223> OTHER INFORMATION: GZMB reverse primer

<400> SEQUENCE: 4
ttatggagct tccccaacag                                                20

<210> SEQ ID NO 5
<211> LENGTH: 20
<212> TYPE: DNA
<213> ORGANISM: Artificial Sequence
<220> FEATURE:
<223> OTHER INFORMATION: WARS forward primer

<400> SEQUENCE: 5
ttgtggaccc atggacagta                                                20

<210> SEQ ID NO 6
<211> LENGTH: 20
<212> TYPE: DNA
<213> ORGANISM: Artificial Sequence
<220> FEATURE:
<223> OTHER INFORMATION: WARS reverse primer

<400> SEQUENCE: 6
ccaaaccgaa caatgagctt                                                20

<210> SEQ ID NO 7
<211> LENGTH: 20
<212> TYPE: DNA
<213> ORGANISM: Artificial Sequence
<220> FEATURE:
<223> OTHER INFORMATION: CDX1 forward primer

<400> SEQUENCE: 7
agggaggaac gtggtcaact                                                20

<210> SEQ ID NO 8
<211> LENGTH: 20
<212> TYPE: DNA
<213> ORGANISM: Artificial Sequence
<220> FEATURE:
<223> OTHER INFORMATION: CDX1 reverse primer

<400> SEQUENCE: 8
tatgatgggg gcaggtagaa                                                20

<210> SEQ ID NO 9
<211> LENGTH: 20
<212> TYPE: DNA
<213> ORGANISM: Artificial Sequence
<220> FEATURE:
<223> OTHER INFORMATION: ACTB forward primer

<400> SEQUENCE: 9
tcaccctgaa gtaccccatc                                                20

<210> SEQ ID NO 10
<211> LENGTH: 20
<212> TYPE: DNA

<213> ORGANISM: Artificial Sequence
<220> FEATURE:
<223> OTHER INFORMATION: ACTB reverse primer

<400> SEQUENCE: 10
tgtggtgcca gattttctcc                                               20

<210> SEQ ID NO 11
<211> LENGTH: 20
<212> TYPE: DNA
<213> ORGANISM: Artificial Sequence
<220> FEATURE:
<223> OTHER INFORMATION: ATP5E forward primer

<400> SEQUENCE: 11
atggtggcct actggagaca                                               20

<210> SEQ ID NO 12
<211> LENGTH: 21
<212> TYPE: DNA
<213> ORGANISM: Artificial Sequence
<220> FEATURE:
<223> OTHER INFORMATION: ATP5E reverse primer

<400> SEQUENCE: 12
ctctcactgc ttttgcacag a                                             21

<210> SEQ ID NO 13
<211> LENGTH: 21
<212> TYPE: DNA
<213> ORGANISM: Artificial Sequence
<220> FEATURE:
<223> OTHER INFORMATION: HPRT1 forward primer

<400> SEQUENCE: 13
tggtcaggca gtataatcca a                                             21

<210> SEQ ID NO 14
<211> LENGTH: 20
<212> TYPE: DNA
<213> ORGANISM: Artificial Sequence
<220> FEATURE:
<223> OTHER INFORMATION: HPRT1 reverse primer

<400> SEQUENCE: 14
cttcgtgggg tccttttcac                                               20

<210> SEQ ID NO 15
<211> LENGTH: 18
<212> TYPE: DNA
<213> ORGANISM: Artificial Sequence
<220> FEATURE:
<223> OTHER INFORMATION: GPX1 forward primer

<400> SEQUENCE: 15
cccgtgcaac cagtttgg                                                 18

<210> SEQ ID NO 16
<211> LENGTH: 23
<212> TYPE: DNA
<213> ORGANISM: Artificial Sequence
<220> FEATURE:
<223> OTHER INFORMATION: GPX1 reverse primer

<400> SEQUENCE: 16
ggacgtactt gagggaattc aga                                           23

<210> SEQ ID NO 17
<211> LENGTH: 20
<212> TYPE: DNA
<213> ORGANISM: Artificial Sequence
<220> FEATURE:
<223> OTHER INFORMATION: UBB forward primer

<400> SEQUENCE: 17
tgggtgagct tgtttgtgtc                                           20

<210> SEQ ID NO 18
<211> LENGTH: 21
<212> TYPE: DNA
<213> ORGANISM: Artificial Sequence
<220> FEATURE:
<223> OTHER INFORMATION: UBB reverse primer

<400> SEQUENCE: 18
tttgacctgt tagcggatac c                                         21

<210> SEQ ID NO 19
<211> LENGTH: 20
<212> TYPE: DNA
<213> ORGANISM: Artificial Sequence
<220> FEATURE:
<223> OTHER INFORMATION: SFRP4 probe

<400> SEQUENCE: 19
aggcaatgcc cagcctcatc                                           20

<210> SEQ ID NO 20
<211> LENGTH: 21
<212> TYPE: DNA
<213> ORGANISM: Artificial Sequence
<220> FEATURE:
<223> OTHER INFORMATION: GZMB probe

<400> SEQUENCE: 20
cgacttcgtg ctgacagctg c                                         21

<210> SEQ ID NO 21
<211> LENGTH: 22
<212> TYPE: DNA
<213> ORGANISM: Artificial Sequence
<220> FEATURE:
<223> OTHER INFORMATION: WARS probe

<400> SEQUENCE: 21 tgcctttgc actgcttgtc tg                                         22

<210> SEQ ID NO 22
<211> LENGTH: 20
<212> TYPE: DNA
<213> ORGANISM: Artificial Sequence
<220> FEATURE:
<223> OTHER INFORMATION: CDX1 probe

<400> SEQUENCE: 22
tgcctcttcc tgcagcctca                                           20

<210> SEQ ID NO 23
<211> LENGTH: 20
<212> TYPE: DNA
<213> ORGANISM: Artificial Sequence
<220> FEATURE:

```
<223> OTHER INFORMATION: ACTB probe

<400> SEQUENCE: 23
cggcatcgtc accaactggg                                               20

<210> SEQ ID NO 24
<211> LENGTH: 27
<212> TYPE: DNA
<213> ORGANISM: Artificial Sequence
<220> FEATURE:
<223> OTHER INFORMATION: ATP5E probe

<400> SEQUENCE: 24
tggactcagc tacatccgat actccca                                       27

<210> SEQ ID NO 25
<211> LENGTH: 21
<212> TYPE: DNA
<213> ORGANISM: Artificial Sequence
<220> FEATURE:
<223> OTHER INFORMATION: HPRT1 probe

<400> SEQUENCE: 25
tgcaagcttg cgaccttgac c                                             21

<210> SEQ ID NO 26
<211> LENGTH: 27
<212> TYPE: DNA
<213> ORGANISM: Artificial Sequence
<220> FEATURE:
<223> OTHER INFORMATION: GPX1 probe

<400> SEQUENCE: 26
ctcttcgttc ttggcgttct cctgatg                                       27

<210> SEQ ID NO 27
<211> LENGTH: 20
<212> TYPE: DNA
<213> ORGANISM: Artificial Sequence
<220> FEATURE:
<223> OTHER INFORMATION: UBB probe

<400> SEQUENCE: 27
caccaaccac gtccacccac                                               20
```